(12) United States Patent
Maney, Jr. et al.

(10) Patent No.: US 11,585,784 B2
(45) Date of Patent: Feb. 21, 2023

(54) PHASED NANOPORE ARRAY

(71) Applicant: Roche Sequencing Solutions, Inc., Pleasanton, CA (US)

(72) Inventors: J. William Maney, Jr., Emerald Hills, CA (US); Santiago Fernandez-Gomez, Sunnyvale, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 195 days.

(21) Appl. No.: 17/170,059

(22) Filed: Feb. 8, 2021

(65) Prior Publication Data

US 2021/0262978 A1 Aug. 26, 2021

Related U.S. Application Data

(63) Continuation of application No. 15/953,303, filed on Apr. 13, 2018, now Pat. No. 10,921,284.

(60) Provisional application No. 62/487,397, filed on Apr. 19, 2017.

(51) Int. Cl.
*G01N 27/447* (2006.01)
*C12Q 1/6874* (2018.01)
*G01N 33/487* (2006.01)

(52) U.S. Cl.
CPC ..... *G01N 27/44717* (2013.01); *C12Q 1/6874* (2013.01); *G01N 27/447* (2013.01); *G01N 27/44713* (2013.01); *G01N 27/44791* (2013.01); *G01N 33/48721* (2013.01)

(58) Field of Classification Search
CPC .......... G01N 27/447; G01N 27/44713; G01N 27/44717; G01N 27/44791; G01N 33/48721; C12Q 1/6874
See application file for complete search history.

(56) References Cited

U.S. PATENT DOCUMENTS

| | | | |
|---|---|---|---|
| 7,731,826 B2 | 6/2010 | Hibbs et al. | |
| 7,835,870 B2 | 11/2010 | Nair et al. | |
| 8,324,914 B2 | 12/2012 | Chen et al. | |
| 8,461,854 B2 | 6/2013 | Chen et al. | |
| 9,290,805 B2 | 3/2016 | Deierling et al. | |
| 9,377,437 B2 | 6/2016 | Chen et al. | |
| 2014/0134616 A1 | 5/2014 | Davis et al. | |
| 2016/0178554 A1 | 6/2016 | Chen et al. | |

(Continued)

OTHER PUBLICATIONS

Horhota, et al.; "Glycerol Nucleoside Triphosphates: Synthesis and Polymerase Substrate Activities"; *Organic Letters*: vol. 8, No. 23, 2006; pp. 5345-5347.

*Primary Examiner* — Luan V Van
*Assistant Examiner* — Caitlyn Mingyun Sun
(74) *Attorney, Agent, or Firm* — Kilpatrick Townsend and Stockton LLP

(57) ABSTRACT

Techniques described herein can apply AC signals with different phases to different groups of nanopore cells in a nanopore sensor chip. When a first group of nanopore cells is in a dark period and is not sampled or minimally sampled by an analog-to-digital converter (ADC) to capture useful data, a second group of nanopore cells is in a bright period during which output signals from the second group of nanopore cells are sampled by the analog-to-digital converter. The reference level setting of the ADC is dynamically changed based on the applied AC signals to fully utilize the dynamic range of the ADC.

16 Claims, 16 Drawing Sheets

(56) References Cited

U.S. PATENT DOCUMENTS

| | | |
|---|---|---|
| 2016/0178577 A1 | 6/2016 | Chen et al. |
| 2016/0367988 A1 | 12/2016 | Azpiroz et al. |
| 2017/0089857 A1 | 3/2017 | Maney et al. |
| 2017/0089858 A1* | 3/2017 | Fernandez-Gomez ............... G01N 27/40 |
| 2017/0091381 A1 | 3/2017 | Fernandez-Gomez et al. |
| 2017/0283866 A1 | 10/2017 | Wahba et al. |
| 2017/0283867 A1 | 10/2017 | Wahba et al. |

* cited by examiner

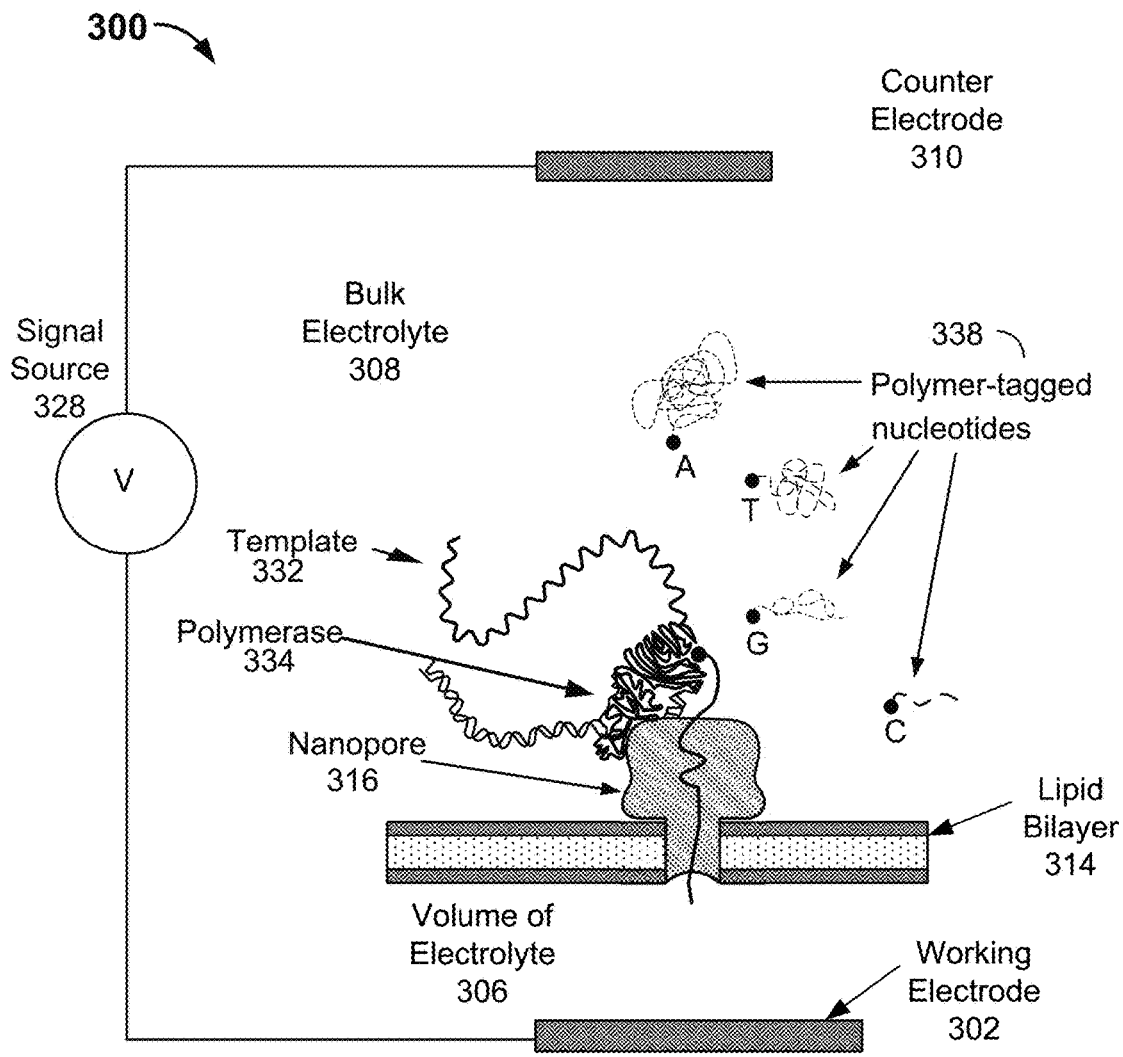
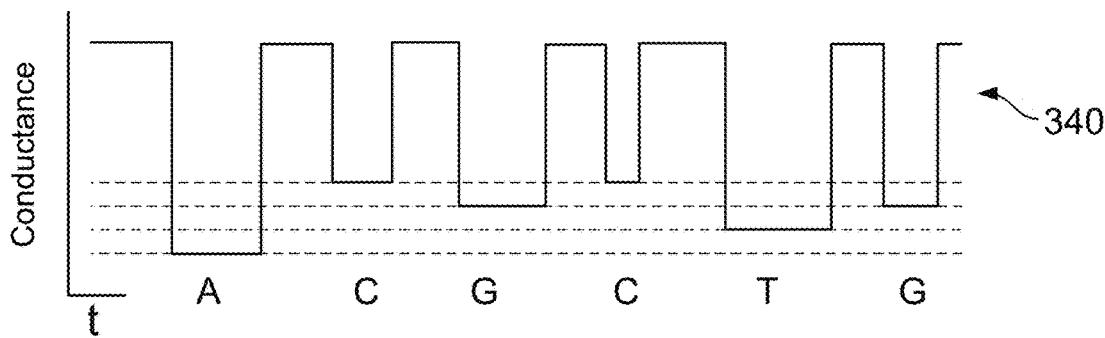
FIG. 3

PHASED NANOPORE ARRAY

CROSS-REFERENCES TO RELATED APPLICATIONS

This application is a continuation of U.S. application Ser. No. 15/953,303, filed on Apr. 13, 2018, which claims priority to U.S. Provisional Application No. 62/487,397, filed on Apr. 19, 2017, the entire contents of each of which is incorporated by reference herein for all purposes.

BACKGROUND

Nanopore membrane devices having pore sizes on the order of one nanometer in internal diameter have shown promise in rapid nucleotide sequencing. When a voltage signal is applied across a nanopore immersed in a conducting fluid, the electric field can move ions in the conducting fluid through the nanopore. The movement of ions in the conducting fluid through the nanopore can cause a small ion current. The voltage applied can also move the molecules to be sequenced into, through, or out of the nanopore. The level of the ion current (or a corresponding voltage) depends on the sizes and chemical structures of the nanopore and the particular molecule that has been moved into the nanopore.

As an alternative to a DNA molecule (or other nucleic acid molecule to be sequenced) moving through the nanopore, a molecule (e.g., a nucleotide being added to a DNA strand) can include a particular tag of a particular size and/or structure. The ion current or a voltage in a circuit including the nanopore (e.g., at an integrating capacitor) can be measured as a way of measuring the resistance of the nanopore corresponding to the molecule, thereby allowing the detection of the particular molecule in the nanopore, and the particular nucleotide at a particular position of a nucleic acid.

A nanopore-based sequencing sensor chip can incorporate a large number of sensor cells configured as an array for parallel DNA sequencing. For example, a nanopore-based sequencing sensor chip may include 100,000 or more cells arranged in a two-dimensional array for sequencing 100,000 or more DNA molecules in parallel. It can be difficult to fit so many cells into a sensor chip without compromising measurements. It can also be difficult to efficiently operate the circuitry on such a sensor chip.

BRIEF SUMMARY

Techniques described herein relate to applying AC signals with different phases to different groups of nanopore cells that are served by a same data sampling circuit in a nanopore sensor chip. Due to the different phases of the AC signals, during a certain time period, a first group of nanopore cells may be in a dark period and is not sampled or minimally sampled by a data sample circuit (e.g., an analog-to-digital converter (ADC)) to capture useful data, while a second group of nanopore cells may be in a bright period and output signals from the second group of nanopore cells may be sampled by the analog-to-digital converter. The reference level setting of the ADC may be dynamically changed based on the applied AC signals to fully utilize the dynamic range of the ADC. The techniques described herein can also be applied to systems that use periodically changing DC bias, which may also have a "dark" period when the electrode is recharged.

According to one embodiment, a sensor chip for nucleic acid (e.g., DNA) sequencing includes a first set of cells organized into N groups, where N is an integer of two or more. Each cell includes a cell electrode that is configured to provide an AC signal to the cell for characterizing a nucleotide of a nucleic acid molecule. The sensor chip for nucleic acid sequencing also includes at least N circuits, where each circuit of the at least N circuits is configured to provide a separately configurable AC signal to one or more cell electrodes of a respective group of cells of the N groups of cells.

According to another embodiment, a sensor chip for nucleic acid sequencing includes a set of cells. Each cell of the set of cells may include a nanopore configured to receive a tag connected to a nucleotide; a membrane within which the nanopore resides, wherein the membrane functions as a capacitor and the nanopore as a resistor in a circuit; a first electrode electrically coupled to circuit on a first end of the cell; and a second electrode coupled to the circuit on a second end of the cell and shared by two or more cells of the set of cells. The sensor chip also includes a control circuit configured to apply a first AC signal through the first electrode to pre-charge the capacitor, and apply a second signal through the second electrode to charge or discharge the pre-charged capacitor via the nanopore.

According to another embodiment, a method of nucleic acid sequencing using a sensor chip including a set of cells may include applying a first AC signal to a first group of cells of the set of cells, and applying a second AC signal to a second group of cells of the set of cells, wherein the first AC signal and the second AC signal have different phases. The method may also include, during a first portion of the first AC signal, sampling, using an analog-to-digital converter (ADC), output signals from the first group of cells and not sampling output signals from the second group of cells. The method may further include, during a second portion of the first AC signal, sampling, using the ADC, output signals from the second group of cells and not sampling the output signals from the first group of cells.

These and other embodiments of the invention are described in detail below. For example, other embodiments are directed to systems, devices, and computer readable media associated with methods described herein.

A better understanding of the nature and advantages of embodiments of the present invention may be gained with reference to the following detailed description and the accompanying drawings

BRIEF DESCRIPTION OF THE DRAWINGS

FIG. 3 illustrates an embodiment of a nanopore cell performing nucleotide sequencing using a nanopore-based sequencing-by-synthesis (Nano-SBS) technique.

DEFINITIONS

Figure 1:
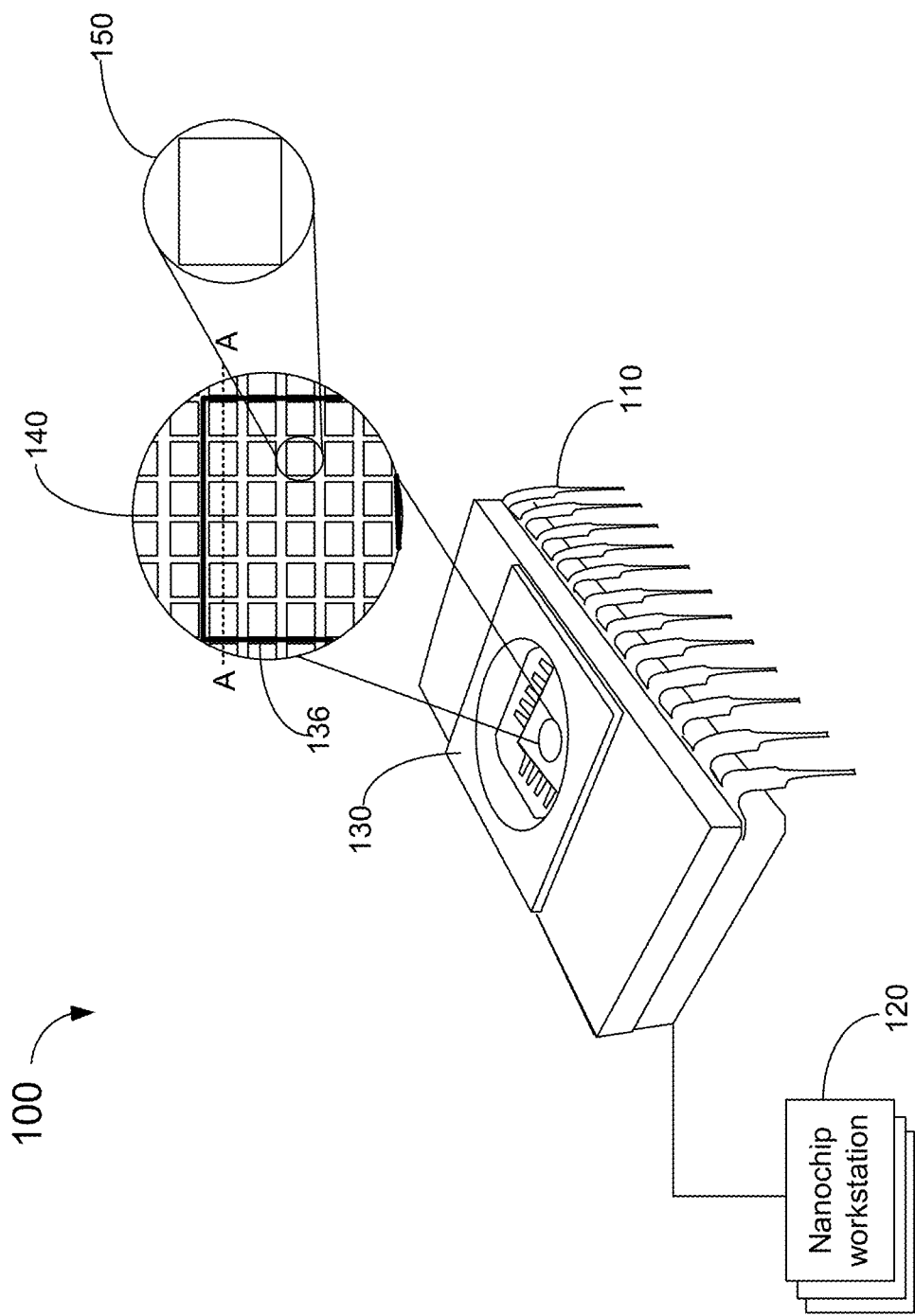
FIG. 1 is a top view of an embodiment of a nanopore sensor chip having an array of nanopore cells.

"Nucleic acid" may refer to deoxyribonucleotides or ribonucleotides and polymers thereof in either single- or double-stranded form. The term may encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs may include, without limitation, phosphorothioates, phosphoramidites, methyl phosphonates, chiral-methyl phosphonates, 2-O-methyl ribonucleotides, peptide-nucleic acids (PNAs). The term nucleic acid may be used interchangeably with gene, cDNA, mRNA, oligonucleotide, and polynucleotide.

The term "template" may refer to a single stranded nucleic acid molecule that is copied into a complementary strand of DNA nucleotides for DNA synthesis. In some cases, a template may refer to the sequence of DNA that is copied during the synthesis of mRNA.

The term "primer" may refer to a short nucleic acid sequence that provides a starting point for DNA synthesis. Enzymes that catalyze the DNA synthesis, such as DNA polymerases, can add new nucleotides to a primer for DNA replication.

As used herein, the term "column" may generally refer to nanopore cells in a nanopore cell array that share a sampling and conversion circuit. Nanopore cells in a column may or may not be physically fabricated in a column on a nanopore sensor chip.

As used herein, the term "bright period" may generally refer to the time period when a tag of a tagged nucleotide is forced into a nanopore by an electric field applied through an AC signal. The term "dark period" may generally refer to the time period when a tag of a tagged nucleotide is pushed out of the nanopore by the electric field applied through the AC signal. An AC cycle may include the bright period and the dark period. In different embodiments, the polarity of the voltage signal applied to a nanopore cell to put the nanopore cell into the bright period (or the dark period) may be different.

DETAILED DESCRIPTION

Techniques disclosed herein relate to nanopore-based nucleic acid sequencing, and more specifically, to increasing data sampling rate by a nanopore-based sequencing sensor chip that includes a large number of parallel sequencing nanopore cells.

In nanopore-based sequencing-by-synthesis (Nano-SBS), higher sampling rates are generally desired because, for example, a higher sampling rate allows the observation of events having shorter durations, which can increase accuracy for base calling. Examples of such events can include an unbound nucleotide tag briefly entering the nanopore, the nucleotide being bound briefly but not getting catalyzed, and a nucleotide getting catalyzed quickly (potentially followed by the same nucleotide getting catalyzed at the next position). However, there is an upper limit to the possible sampling rate due to, for example, limited sampling and conversion speed of analog-to-digital convertors, and/or limited bandwidth of buses, data storage devices, or data processing circuits.

AC signals may be used in Nano-SBS to improve the lifetime of a nanopore sensor chip including an array of nanopore cells. For example, a constant level may be applied to the working electrode of each nanopore cell in the nanopore sensor chip, and a universal AC signal may be applied to a shared counter electrode of the nanopore cells. In this example, each nanopore cell goes through the AC cycles at substantially the same phase. Each AC cycle may include a bright period (a tag may be pushed into a nanopore for identifying a nucleotide) and a dark period, where the duty cycle may be low (i.e., the dark period may be much longer than the bright period). Thus, all nanopore cells of the nanopore sensor chip would be in the bright period or the dark period at roughly the same time.

During the bright period, a data sampling and conversion circuit associated with nanopore cells in a column can sequentially sample and convert output voltage signals from each nanopore cell in the column, as part of identifying a tag and consequently a nucleotide being incorporated. The AC signal attracts (threads) a bound nucleotide tag into the nanopore in the bright period, and thus the measured signals provide information about which tag (and thus which nucleotide) is currently bound. During the dark period (any nucleotide tag is pushed out of the nanopore), information about any nucleotide tag in the nanopore is unobtainable and thus the output voltage signals from the cells have little or no use. Yet, during the dark period, output voltage signals from the cells may still be sampled and converted anyway, or the data sampling and conversion circuit may be idle. Thus, a significant portion of the bandwidth of the data sampling and conversion circuit may not be utilized to capture useful data at least during the dark period.

Further, for nanopore sensor chips with a high cell density, a single sampling and conversion circuit may service multiple cells. Thus, each cell may be sampled at a rate much lower than the full sampling rate of the sampling and conversion circuit.

Techniques disclosed herein address the above issues by applying AC signals with different phases to different nanopore cells in a column, such that, when some nanopore cells in the column are in the dark period, some other nanopore cells in the same column are in the bright period. For example, the nanopore cells in a column may be organized into two or more groups. A constant voltage level may be applied to the counter electrodes of all nanopore cells, and the phase of an AC signal applied to the working electrodes of nanopore cells in each group of nanopore cells may be delayed by a different value.

In this way, at any given time, the data sampling and conversion circuit may sample and convert the output voltage signals from the portion of the nanopore cells in the column that are in the bright period, with the dark period being sampled minimally, e.g., for normalization purposes only. As such, the data sampling and conversion can be performed at a higher rate for each nanopore cell during the bright period, since the circuit is servicing fewer cells at any given time. Furthermore, because the dark period is only minimally sampled, all or almost all of the data captured would be useful, as opposed to the instance where the dark period is being sampled at an unnecessarily high rate. In this way, embodiments can reduce the number of cells being serviced by the sampling and conversion circuit in any period of time, and thus increase the sampling rate per cell even without using a faster data sampling and conversion circuit.

I. Nanopore Based Sequencing Chip

FIG. 1 is a top view of an embodiment of a nanopore sensor chip 100 having an array 140 of nanopore cells 150. Each nanopore cell 150 includes a control circuit integrated on a silicon substrate of nanopore sensor chip 100. In some embodiments, side walls 136 may be included in array 140 to separate groups of nanopore cells 150 so that each group may receive a different sample for characterization. Each nanopore cell may be used to sequence a nucleic acid.

In some embodiments, nanopore sensor chip 100 may include a cover plate 130. In some embodiments, nanopore sensor chip 100 may also include a plurality of pins 110 for interfacing with other circuits, such as a computer processor.

In some embodiments, nanopore sensor chip 100 may include multiple chips in a same package, such as, for example, a Multi-Chip Module (MCM) or System-in-Package (SiP). The chips may include, for example, a memory, a processor, a field-programmable gate array (FPGA), an application-specific integrated circuit (ASIC), data converters, a high-speed I/O interface, etc.

In some embodiments, nanopore sensor chip 100 may be coupled to (e.g., docked to) a nanochip workstation 120, which may include various components for carrying out (e.g., automatically carrying out) various embodiments of the processes disclosed herein, including, for example, analyte delivery mechanisms, such as pipettes for delivering lipid suspension or other membrane structure suspension, analyte solution, and/or other liquids, suspension or solids, robotic arms, computer processor, and/or memory. A plurality of polynucleotides may be detected on array 140 of nanopore cells 150. In some embodiments, each nanopore cell 150 can be individually addressable.

II. Nanopore Sequencing Cell

Nanopore cells 150 in nanopore sensor chip 100 may be implemented in many different ways. For example, in some embodiments, tags of different sizes and/or chemical structures may be attached to different nucleotides in a nucleic acid molecule to be sequenced. In some embodiments, a complementary strand to a template of the nucleic acid molecule to be sequenced may be synthesized by hybridizing differently polymer-tagged nucleotides with the template. In some implementations, the nucleic acid molecule and the attached tags may both move through the nanopore, and an ion current passing through the nanopore may indicate the nucleotide that is in the nanopore because of the particular size and/or structure of the tag attached to the nucleotide. In some implementations, only the tags may be moved into the nanopore. There may also be many different ways to detect the different tags in the nanopores.

A. Nanopore Sequencing Cell Structure

Figure 2:
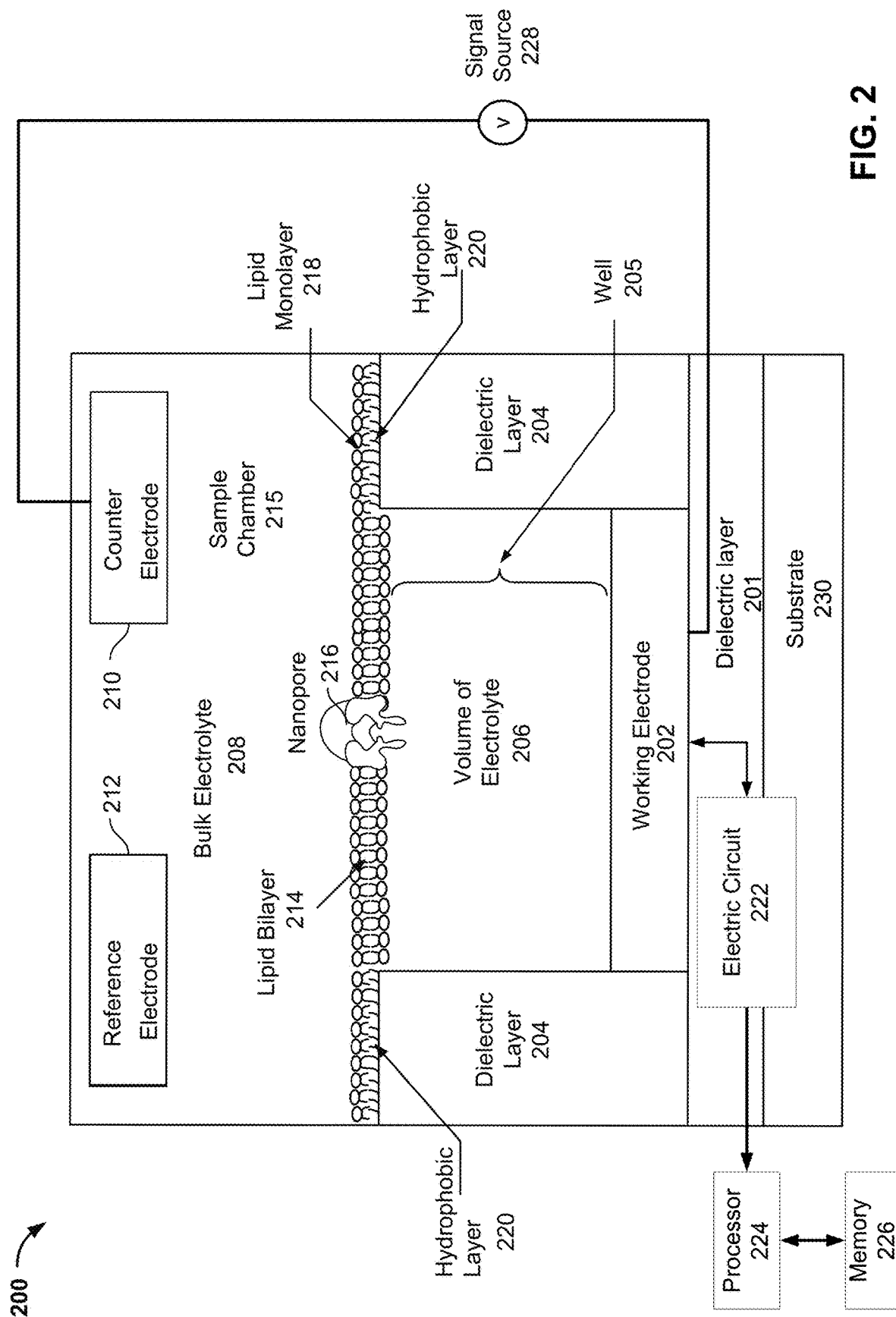
FIG. 2 illustrates an embodiment of a nanopore cell in a nanopore sensor chip that can be used to characterize a polynucleotide or a polypeptide.

FIG. 2 illustrates an embodiment of an example nanopore cell 200 in a nanopore sensor chip, such as nanopore cell 150 in nanopore sensor chip 100 of FIG. 1, that can be used to characterize a polynucleotide or a polypeptide. Nanopore cell 200 may include a well 205 formed of dielectric layers 201 and 204; a membrane, such as a lipid bilayer 214 formed over well 205; and a sample chamber 215 on lipid bilayer 214 and separated from well 205 by lipid bilayer 214. Well 205 may contain a volume of electrolyte 206, and sample chamber 215 may hold bulk electrolyte 208 containing a nanopore, e.g., a soluble protein nanopore transmembrane molecular complexes (PNTMC), and the analyte of interest (e.g., a nucleic acid molecule to be sequenced).

Nanopore cell 200 may include a working electrode 202 at the bottom of well 205 and a counter electrode 210 disposed in sample chamber 215. A signal source 228 may apply a voltage signal between working electrode 202 and counter electrode 210. A single nanopore (e.g., a PNTMC) may be inserted into lipid bilayer 214 by an electroporation process caused by the voltage signal, thereby forming a nanopore 216 in lipid bilayer 214. The individual membranes (e.g., lipid bilayers 214 or other membrane structures) in the array may be neither chemically nor electrically connected to each other. Thus, each nanopore cell in the array may be an independent sequencing machine, producing data unique to the single polymer molecule associated with the nanopore that operates on the analyte of interest and modulates the ionic current through the otherwise impermeable lipid bilayer.

As shown in FIG. 2, nanopore cell 200 may be formed on a substrate 230, such as a silicon substrate. Dielectric layer 201 may be formed on substrate 230. Dielectric material used to form dielectric layer 201 may include, for example, glass, oxides, nitrides, and the like. An electric circuit 222 for controlling electrical stimulation and for processing the signal detected from nanopore cell 200 may be formed on substrate 230 and/or within dielectric layer 201. For example, a plurality of patterned metal layers (e.g., metal 1 to metal 6) may be formed in dielectric layer 201, and a plurality of active devices (e.g., transistors) may be fabricated on substrate 230. In some embodiments, signal source 228 is included as a part of electric circuit 222. Electric circuit 222 may include, for example, amplifiers, integrators, analog-to-digital converters, noise filters, feedback control logic, and/or various other components. Electric circuit 222 may be further coupled to a processor 224 that is coupled to a memory 226, where processor 224 can analyze the sequencing data to determine sequences of the polymer molecules that have been sequenced in the array.

Working electrode 202 may be formed on dielectric layer 201, and may form at least a part of the bottom of well 205. In some embodiments, working electrode 202 is a metal electrode. For non-faradaic conduction, working electrode 202 may be made of metals or other materials that are resistant to corrosion and oxidation, such as, for example, platinum, gold, titanium nitride, and graphite. For example, working electrode 202 may be a platinum electrode with electroplated platinum. In another example, working electrode 202 may be a titanium nitride (TiN) working electrode. Working electrode 202 may be porous, thereby increasing its surface area and a resulting capacitance associated with working electrode 202. Because the working electrode of a nanopore cell may be independent from the working electrode of another nanopore cell, the working electrode may be referred to as cell electrode in this disclosure.

Dielectric layer 204 may be formed above dielectric layer 201. Dielectric layer 204 forms the walls surrounding well 205. Dielectric material used to form dielectric layer 204 may include, for example, glass, oxide, silicon mononitride (SiN), polyimide, or other suitable hydrophobic insulating material. The top surface of dielectric layer 204 may be silanized. The silanization may form a hydrophobic layer 220 above the top surface of dielectric layer 204. In some embodiments, hydrophobic layer 220 has a thickness of about 1.5 nanometer (nm).

Well 205 formed by the dielectric layer walls 204 includes volume of electrolyte 206 above working electrode 202. Volume of electrolyte 206 may be buffered and may include one or more of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$)), strontium chloride ($SrCl_2$), manganese chloride ($MnCl_2$), and magnesium chloride ($MgCl_2$). In some embodiments, volume of electrolyte 206 has a thickness of about three microns (μm).

As also shown in FIG. 2, a membrane may be formed on top of dielectric layer 204 and span across well 205. In some embodiments, the membrane may include a lipid monolayer 218 formed on top of hydrophobic layer 220. As the membrane reaches the opening of well 205, lipid monolayer 208 may transition to lipid bilayer 214 that spans across the opening of well 205. The lipid bilayer may comprise or consist of phospholipid, for example, selected from diphytanoyl-phosphatidylcholine (DPhPC), 1,2-diphytanoyl-sn-glycero-3-phosphocholine, 1,2-Di-O-Phytanyl-sn-Glycero-3-phosphocholine (DoPhPC), palmitoyl-oleoyl-phosphatidylcholine (POPC), dioleoyl-phosphatidyl-methylester (DOPME), dipalmitoylphosphatidylcholine (DPPC), phosphatidylcholine, phosphatidylethanolamine, phosphatidylserine, phosphatidic acid, phosphatidylinositol, phosphatidylglycerol, sphingomyelin, 1,2-di-O-phytanyl-sn-glycerol; 1,2-dipalmitoyl-sn-glycero-3-phosphoethanolamine-N-[methoxy(polyethylene glycol)-350]; 1,2-dipalmitoyl-sn-glycero-3-phosphoethanolamine-N-[methoxy (polyethylene glycol)-550]; 1,2-dipalmitoyl-sn-glycero-3-phosphoethanolamine-N-[methoxy(polyethylene glycol)-750]; 1,2-dipalmitoyl-sn-glycero-3-phosphoethanolamine-N-[methoxy(polyethylene glycol)-1000]; 1,2-dipalmitoyl-sn-glycero-3-phosphoethanolamine-N-[methoxy (polyethylene glycol)-2000]; 1,2-dioleoyl-sn-glycero-3-phosphoethanolamine-N-lactosyl; GM1 Ganglioside, Lysophosphatidylcholine (LPC) or any combination thereof.

As shown, lipid bilayer 214 is embedded with a single nanopore 216, e.g., formed by a single PNTMC. As described above, nanopore 216 may be formed by inserting a single PNTMC into lipid bilayer 214 by electroporation. Nanopore 216 may be large enough for passing at least a portion of the analyte of interest and/or small ions (e.g., $Na^+$, $K^+$, $Ca^{2+}$, $Cl^-$) between the two sides of lipid bilayer 214.

Sample chamber 215 is over lipid bilayer 214, and can hold a solution of the analyte of interest for characterization. The solution may be an aqueous solution containing bulk electrolyte 208 and buffered to an optimum ion concentration and maintained at an optimum pH to keep the nanopore 216 open. Nanopore 216 crosses lipid bilayer 214 and provides the only path for ionic flow from bulk electrolyte 208 to working electrode 202. In addition to nanopores (e.g., PNTMCs) and the analyte of interest, bulk electrolyte 208 may further include one or more of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$)), strontium chloride ($SrCl_2$), Manganese chloride ($MnCl_2$), and magnesium chloride ($MgCl_2$).

Counter electrode (CE) 210 may be an electrochemical potential sensor. In some embodiments, counter electrode 210 may be shared between a plurality of nanopore cells, and may therefore be referred to as a common electrode. In some cases, the common potential and the common electrode may be common to all nanopore cells, or at least all nanopore cells within a particular grouping. The common electrode can be configured to apply a common potential to the bulk electrolyte 208 in contact with the nanopore 216. Counter electrode 210 and working electrode 202 may be coupled to signal source 228 for providing electrical stimulus (e.g., voltage bias) across lipid bilayer 214, and may be used for sensing electrical characteristics of lipid bilayer 214 (e.g., resistance, capacitance, and ionic current flow). In some embodiments, nanopore cell 200 can also include a reference electrode 212.

In some embodiments, various checks can be made during creation of the nanopore cell as part of calibration. Once a nanopore cell is created, further calibration steps can be performed, e.g., to identify nanopore cells that are performing as desired (e.g., one nanopore in the cell). Such calibration checks can include physical checks, voltage calibration, open channel calibration, and identification of cells with a single nanopore.

B. Detection Signals of Nanopore Sequencing Cell

Nanopore cells in nanopore sensor chip, such as nanopore cells 150 in nanopore sensor chip 100, may enable parallel sequencing using a single molecule nanopore-based sequencing by synthesis (Nano-SBS) technique.

FIG. 3 illustrates an embodiment of a nanopore cell 300 performing nucleotide sequencing using the Nano-SBS technique. In the Nano-SBS technique, a template 332 to be sequenced (e.g., a nucleotide acid molecule or another analyte of interest) and a primer may be introduced into bulk electrolyte 308 in the sample chamber of nanopore cell 300. As examples, template 332 can be circular or linear. A nucleic acid primer may be hybridized to a portion of template 332 to which four differently polymer-tagged nucleotides 338 may be added.

In some embodiments, an enzyme (e.g., a polymerase 334, such as a DNA polymerase) may be associated with nanopore 316 for use in the synthesizing a complementary strand to template 332. For example, polymerase 334 may be covalently attached to nanopore 316. Polymerase 334 may catalyze the incorporation of nucleotides 338 onto the primer using a single stranded nucleic acid molecule as the template. Nucleotides 338 may comprise tag species ("tags") with the nucleotide being one of four different types: A, T, G, or C. When a tagged nucleotide is correctly complexed with polymerase 334, the tag may be pulled (loaded) into the nanopore by an electrical force, such as a force generated in the presence of an electric field generated by a voltage applied across lipid bilayer 314 and/or nanopore 316. The tail of the tag may be positioned in the barrel of nanopore 316. The tag held in the barrel of nanopore 316 may generate a unique ionic blockade signal 340 due to the tag's distinct chemical structure and/or size, thereby electronically identifying the added base to which the tag attaches.

As used herein, a "loaded" or "threaded" tag may be one that is positioned in and/or remains in or near the nanopore for an appreciable amount of time, e.g., 0.1 millisecond (ms) to 10000 ms. In some cases, a tag is loaded in the nanopore prior to being released from the nucleotide. In some instances, the probability of a loaded tag passing through (and/or being detected by) the nanopore after being released upon a nucleotide incorporation event is suitably high, e.g., 90% to 99%.

In some embodiments, before polymerase 334 is connected to nanopore 316, the conductance of nanopore 316 may be high, such as, for example, about 300 picosiemens (300 pS). As the tag is loaded in the nanopore, a unique conductance signal (e.g., signal 340) is generated due to the tag's distinct chemical structure and/or size. For example, the conductance of the nanopore can be about 60 pS, 80 pS, 100 pS, or 120 pS, each corresponding to one of the four types of tagged nucleotides. The polymerase may then undergo an isomerization and a transphosphorylation reaction to incorporate the nucleotide into the growing nucleic acid molecule and release the tag molecule.

In some cases, some of the tagged nucleotides may not match (complementary bases) with a current position of the nucleic acid molecule (template). The tagged nucleotides that are not base-paired with the nucleic acid molecule may also pass through the nanopore. These non-paired nucleotides can be rejected by the polymerase within a time scale that is shorter than the time scale for which correctly paired nucleotides remain associated with the polymerase. Tags bound to non-paired nucleotides may pass through the nanopore quickly, and be detected for a short period of time (e.g., less than 10 ms), while tags bounded to paired nucleotides can be loaded into the nanopore and detected for a long period of time (e.g., at least 10 ms). Therefore, non-paired nucleotides may be identified by a downstream processor based at least in part on the time for which the nucleotide is detected in the nanopore.

A conductance (or equivalently the resistance) of the nanopore including the loaded (threaded) tag can be measured via a current passing through the nanopore, thereby providing an identification of the tag species and thus the nucleotide at the current position. In some embodiments, a direct current (DC) signal can be applied to the nanopore cell (e.g., so that the direction at which the tag moves through the nanopore is not reversed). However, operating a nanopore sensor for long periods of time using a direct current can change the composition of the electrode, unbalance the ion concentrations across the nanopore, and have other undesirable effects that can affect the lifetime of the nanopore cell. Applying an alternating current (AC) waveform can reduce the electro-migration to avoid these undesirable effects and have certain advantages as described below. The nucleic acid sequencing methods described herein that utilize tagged nucleotides are fully compatible with applied AC voltages, and therefore an AC waveform can be used to achieve these advantages.

The ability to re-charge the electrode during the AC detection cycle can be advantageous when sacrificial electrodes, electrodes that change molecular character in the current-carrying reactions (e.g., electrodes comprising silver), or electrodes that change molecular character in current-carrying reactions are used. An electrode may deplete during a detection cycle when a direct current signal is used. The recharging can prevent the electrode from reaching a depletion limit, such as becoming fully depleted, which can be a problem when the electrodes are small (e.g., when the electrodes are small enough to provide an array of electrodes having at least 500 electrodes per square millimeter). Electrode lifetime in some cases scales with, and is at least partly dependent on, the width of the electrode.

Suitable conditions for measuring ionic currents passing through the nanopores are known in the art and examples are provided herein. The measurement may be carried out with a voltage applied across the membrane and pore. In some embodiments, the voltage used may range from −400 mV to +400 mV. The voltage used is preferably in a range having a lower limit selected from −400 mV, −300 mV, −200 mV, −150 mV, −100 mV, −50 mV, −20 mV, and 0 mV, and an upper limit independently selected from +10 mV, +20 mV, +50 mV, +100 mV, +150 mV, +200 mV, +300 mV, and +400 mV. The voltage used may be more preferably in the range of 100 mV to 240 mV and most preferably in the range of 160 mV to 240 mV. It is possible to increase discrimination between different nucleotides by a nanopore using an increased applied potential. Sequencing nucleic acids using AC waveforms and tagged nucleotides is described in US Patent Publication No. US 2014/0134616 entitled "Nucleic Acid Sequencing Using Tags," filed on Nov. 6, 2013, which is herein incorporated by reference in its entirety. In addition to the tagged nucleotides described in US 2014/0134616, sequencing can be performed using nucleotide analogs that lack a sugar or acyclic moiety, e.g., (S)-Glycerol nucleoside triphosphates (gNTPs) of the five common nucleobases: adenine, cytosine, guanine, uracil, and thymine (Horhota et al., Organic Letters, 8:5345-5347 [2006]).

C. Electric Circuit of Nanopore Sequencing Cell

Figure 4:
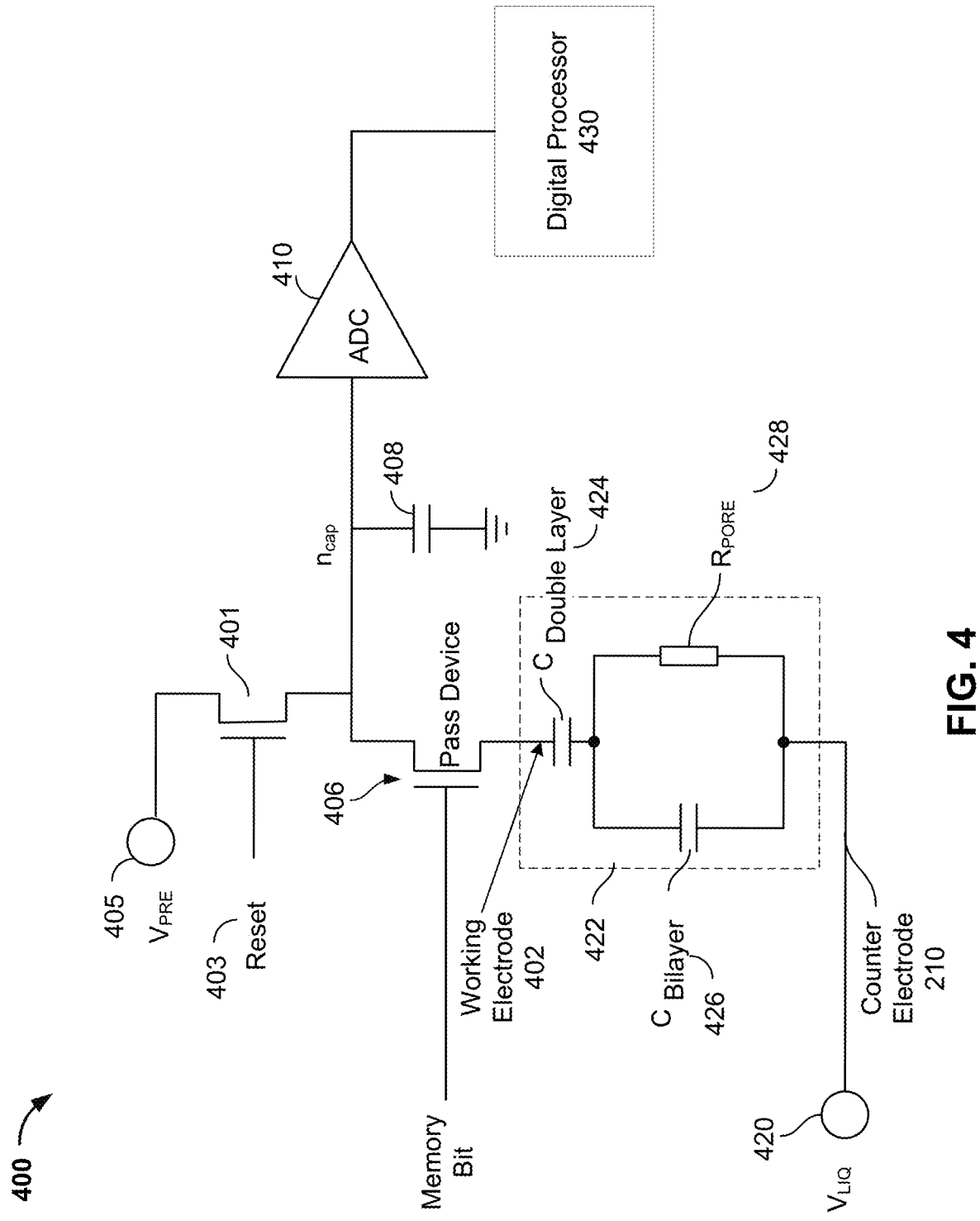
FIG. 4 illustrates an embodiment of an electric circuit in a nanopore cell.

FIG. 4 illustrates an embodiment of an electric circuit 400 (which may include portions of electric circuit 222 in FIG. 2) in a nanopore cell, such as nanopore cell 200. As described above, in some embodiments, electric circuit 400 includes a counter electrode 210 that may be shared between a plurality of nanopore cells or all nanopore cells in a nanopore sensor chip, and may therefore also be referred to as a common electrode. The common electrode can be configured to apply a common potential to the bulk electrolyte (e.g., bulk electrolyte 208) in contact with the lipid bilayer (e.g., lipid bilayer 214) in the nanopore cells by connecting to a voltage source $V_{LIQ}$ 420. In some embodiments, an AC non-Faradaic mode may be utilized to modulate voltage $V_{LIQ}$ with an AC signal (e.g., a square wave) and apply it to the bulk electrolyte in contact with the lipid bilayer in the nanopore cell. In some embodiments, $V_{LIQ}$ is a square wave with a magnitude of ±200-250 mV and a frequency between, for example, 25 and 400 Hz. The bulk electrolyte between counter electrode 210 and the lipid bilayer (e.g., lipid bilayer 214) may be modeled by a large capacitor (not shown), such as, for example, 100 μF or larger.

FIG. 4 also shows an electrical model 422 representing the electrical properties of a working electrode (e.g., working electrode 202) and the lipid bilayer (e.g., lipid bilayer 214). Electrical model 422 includes a capacitor 426 ($C_{Bilayer}$) that models a capacitance associated with the lipid bilayer and a resistor 428 ($R_{PORE}$) that models a variable resistance associated with the nanopore, which can change based on the presence of a particular tag in the nanopore. Electrical model 422 also includes a capacitor 424 having a double layer capacitance ($C_{Double\ Layer}$) and representing the electrical properties of working electrode 202 and well 205. Working electrode 202 may be configured to apply a distinct potential independent from the working electrodes in other nanopore cells.

Pass device 406 is a switch that can be used to connect or disconnect the lipid bilayer and the working electrode from electric circuit 400. Pass device 406 may be controlled by a memory bit to enable or disable a voltage stimulus to be applied across the lipid bilayer in the nanopore cell. Before lipids are deposited to form the lipid bilayer, the impedance between the two electrodes may be very low because the well of the nanopore cell is not sealed, and therefore pass device 406 may be kept open to avoid a short-circuit condition. Pass device 406 may be closed after lipid solvent has been deposited to the nanopore cell to seal the well of the nanopore cell.

Circuitry 400 may further include an on-chip integrating capacitor 408 (ncap). Integrating capacitor 408 may be pre-charged by using a reset signal 403 to close switch 401, such that integrating capacitor 408 is connected to a voltage source $V_{PRE}$ 405. In some embodiments, voltage source $V_{PRE}$ 405 provides a constant positive voltage with a magnitude of, for example, 900 mV. When switch 401 is closed, integrating capacitor 408 may be pre-charged to the positive voltage level of voltage source $V_{PRE}$ 405.

After integrating capacitor 408 is pre-charged, reset signal 403 may be used to open switch 401 such that integrating capacitor 408 is disconnected from voltage source $V_{PRE}$ 405. At this point, depending on the level of voltage source $V_{LIQ}$, the potential of counter electrode 210 may be at a level higher than the potential of working electrode 202 (and integrating capacitor 408), or vice versa. For example, during a positive phase of a square wave from voltage source $V_{LIQ}$ (e.g., the bright or dark period of the AC voltage source signal cycle), the potential of counter electrode 210 is at a level higher than the potential of working electrode 202. During a negative phase of the square wave from voltage source $V_{LIQ}$ (e.g., the dark or bright period of the AC voltage source signal cycle), the potential of counter electrode 210 is at a level lower than the potential of working electrode 202. Thus, in some embodiments, integrating capacitor 408 may be further charged during the bright period from the pre-charged voltage level of voltage source $V_{PRE}$ 405 to a higher level, and discharged during the dark period to a lower level, due to the potential difference between counter electrode 210 and working electrode 202. In other embodiments, the charging and discharging may occur in dark periods and bright periods, respectively.

Integrating capacitor 408 may be charged or discharged for a fixed period of time, depending on the sampling rate of an analog-to-digital converter (ADC) 410, which may be higher than 1 kHz, 5 kHz, 10 kHz, 100 kHz, or more. For example, with a sampling rate of 1 kHz, integrating capacitor 408 may be charged/discharged for a period of about 1 ms, and then the voltage level may be sampled and converted by ADC 410 at the end of the integration period. A particular voltage level would correspond to a particular tag species in the nanopore, and thus correspond to the nucleotide at a current position on the template.

After being sampled by ADC 410, integrating capacitor 408 may be pre-charged again by using reset signal 403 to close switch 401, such that integrating capacitor 408 is connected to voltage source $V_{PRE}$ 405 again. The steps of pre-charging integrating capacitor 408, waiting for a fixed period of time for integrating capacitor 408 to charge or discharge, and sampling and converting the voltage level of integrating capacitor by ADC 410 can be repeated in cycles throughout the sequencing process.

A digital processor 430 can process the ADC output data, e.g., for normalization, data buffering, data filtering, data compression, data reduction, event extraction, or assembling ADC output data from the array of nanopore cells into various data frames. In some embodiments, digital processor 430 can perform further downstream processing, such as base determination. Digital processor 430 can be implemented as hardware (e.g., in a GPU, FPGA, ASIC, etc.) or as a combination of hardware and software.

Accordingly, the voltage signal applied across the nanopore can be used to detect particular states of the nanopore. One of the possible states of the nanopore is an open-channel state when a tag-attached polyphosphate is absent from the barrel of the nanopore. Another four possible states of the nanopore each correspond to a state when one of the four different types of tag-attached polyphosphate nucleotides (A, T, G, or C) is held in the barrel of the nanopore. Yet another possible state of the nanopore is when the lipid bilayer is ruptured.

When the voltage level on integrating capacitor 408 is measured after a fixed period of time, the different states of a nanopore may result in measurements of different voltage levels. This is because the rate of the voltage decay (decrease by discharging or increase by charging) on integrating capacitor 408 (i.e., the steepness of the slope of a voltage on integrating capacitor 408 versus time plot) depends on the nanopore resistance (e.g., the resistance of resistor $R_{PORE}$ 428). More particularly, as the resistance associated with the nanopore in different states is different due to the molecules' (tags') distinct chemical structures, different corresponding rates of voltage decay may be observed and may be used to identify the different states of the nanopore. The voltage decay curve may be an exponential curve with an RC time constant $\tau=RC$, where R is the resistance associated with the nanopore (i.e., $R_{PORE}$ 428) and C is the capacitance associated with the membrane (i.e., capacitor 426 ($C_{Bilayer}$)) in parallel with R. A time constant of the nanopore cell can be, for example, about 200-500 ms. The decay curve may not fit exactly to an exponential curve due to the detailed implementation of the bilayer, but the decay curve may be similar to an exponential curve and is monotonic, thus allowing detection of tags.

In some embodiments, the resistance associated with the nanopore in an open-channel state may be in the range of 100 MOhm to 20 GOhm. In some embodiments, the resistance associated with the nanopore in a state where a tag is inside the barrel of the nanopore may be within the range of 200 MOhm to 40 GOhm. In other embodiments, integrating capacitor 408 may be omitted, as the voltage leading to ADC 410 will still vary due to the voltage decay in electrical model 422.

The rate of the decay of the voltage on integrating capacitor 408 may be determined in different ways. As explained above, the rate of the voltage decay may be determined by measuring a voltage decay during a fixed time interval. For example, the voltage on integrating capacitor 408 may be first measured by ADC 410 at time t1, and then the voltage is measured again by ADC 410 at time t2. The voltage difference is greater when the slope of the voltage on integrating capacitor 408 versus time curve is steeper, and the voltage difference is smaller when the slope of the voltage curve is less steep. Thus, the voltage difference may be used as a metric for determining the rate of the decay of the voltage on integrating capacitor 408, and thus the state of the nanopore cell.

In other embodiments, the rate of the voltage decay can be determined by measuring a time duration that is required for a selected amount of voltage decay. For example, the time required for the voltage to drop or increase from a first voltage level V1 to a second voltage level V2 may be measured. The time required is less when the slope of the voltage vs. time curve is steeper, and the time required is greater when the slope of the voltage vs. time curve is less steep. Thus, the measured time required may be used as a metric for determining the rate of the decay of the voltage on integrating capacitor $n_{cap}$ 408, and thus the state of the nanopore cell. One skilled in the art will appreciate the various circuits that can be used to measure the resistance of the nanopore, e.g., including current measurement techniques.

In some embodiments, electric circuit 400 may not include a pass device (e.g., pass device 406) and an extra capacitor (e.g., integrating capacitor 408 ($n_{cap}$)) that are fabricated on-chip, thereby facilitating the reduction in size of the nanopore-based sequencing chip. Due to the thin nature of the membrane (lipid bilayer), the capacitance associated with the membrane (e.g., capacitor 426 ($C_{Bilayer}$)) alone can suffice to create the required RC time constant without the need for additional on-chip capacitance. Therefore, capacitor 426 may be used as the integrating capacitor, and may be pre-charged by the voltage signal $V_{PRE}$ and subsequently be discharged or charged by the voltage signal $V_{LIQ}$. The elimination of the extra capacitor and the pass device that are otherwise fabricated on-chip in the electric circuit can significantly reduce the footprint of a single nanopore cell in the nanopore sequencing chip, thereby facilitating the scaling of the nanopore sequencing chip to include more and more cells (e.g., having millions of cells in a nanopore sequencing chip).

D. Data sampling in nanopore cell

To perform sequencing of a nucleic acid, the voltage level of integrating capacitor (e.g., integrating capacitor 408 ($n_{cap}$) or capacitor 426 ($C_{Bilayer}$)) can be sampled and converted by the ADC (e.g., ADC 410) while a tagged nucleotide is being added to the nucleic acid. The tag of the nucleotide can be pushed into the barrel of the nanopore by the electric field across the nanopore that is applied through the counter electrode and the working electrode, for example, when the applied voltage is such that $V_{LIQ}$ is lower than $V_{PRE}$.

1. Threading

A threading event is when a tagged nucleotide is attached to the template (e.g., nucleic acid fragment), and the tag goes in and out of the barrel of the nanopore. This can happen multiple times during a threading event. When the tag is in the barrel of the nanopore, the resistance of the nanopore may be higher, and a lower current may flow through the nanopore.

During sequencing, a tag may not be in the nanopore in some AC cycles (referred to as an open-channel state), where the current is the highest because of the lower resistance of the nanopore. When a tag is attracted into the barrel of the nanopore, the nanopore is in a bright mode. When the tag is pushed out of the barrel of the nanopore, the nanopore is in a dark mode.

2. Bright and Dark Period

During an AC cycle, the voltage on integrating capacitor may be sampled multiple times by the ADC. For example, in one embodiment, an AC voltage signal is applied across the system at, e.g., about 100 Hz, and an acquisition rate of the ADC can be about 2000 Hz per cell. Thus, there can be about 20 data points (voltage measurements) captured per AC cycle (cycle of an AC waveform). Data points corresponding to one cycle of the AC waveform may be referred to as a set. In a set of data points for an AC cycle, there may be a subset captured when, for example, $V_{LIQ}$ is lower than $V_{PRE}$, which may correspond to a bright mode (period) where the tag is forced into the barrel of the nanopore. Another subset may correspond to a dark mode (period) where the tag is pushed out of the barrel of the nanopore by the applied electric field when, for example, $V_{LIQ}$ is higher than $V_{PRE}$.

3. Measured Voltages

For each data point, when the switch 401 is opened, the voltage at the integrating capacitor (e.g., integrating capacitor 408 ($n_{cap}$) or capacitor 426 ($C_{Bilayer}$)) will change in a decaying manner as a result of the charging/discharging by $V_{LIQ}$, e.g., as an increase from $V_{PRE}$ to $V_{LIQ}$ when $V_{LIQ}$ is higher than $V_{PRE}$ or a decrease from $V_{PRE}$ to $V_{LIQ}$ when $V_{LIQ}$ is lower than $V_{PRE}$. The final voltage values may deviate from $V_{LIQ}$ as the working electrode charges. The rate of change of the voltage level on the integrating capacitor may be governed by the value of the resistance of the bilayer, which may include the nanopore, which may in turn include a molecule (e.g., a tag of a tagged nucleotides) in the nanopore. The voltage level can be measured at a predetermined time after switch 401 opens.

Switch 401 may operate at the rate of data acquisition. Switch 401 may be closed for a relatively short time period between two acquisitions of data, typically right after a measurement by the ADC. The switch allows multiple data points to be collected for each cycle. If switch 401 remains open, the voltage level on the integrating capacitor, and thus the output value of the ADC, would fully decay and stay there. Such multiple measurements can allow higher resolution with a fixed ADC (e.g. 8-bit to 14-bit due to the greater number of measurements, which may be averaged). The multiple measurements can also provide kinetic information about the molecule threaded into the nanopore. The timing information may allow the determination of how long a threading takes place. This can also be used in helping to determine whether multiple nucleotides that are added to the nucleic acid strand are being sequenced.

Figure 5:
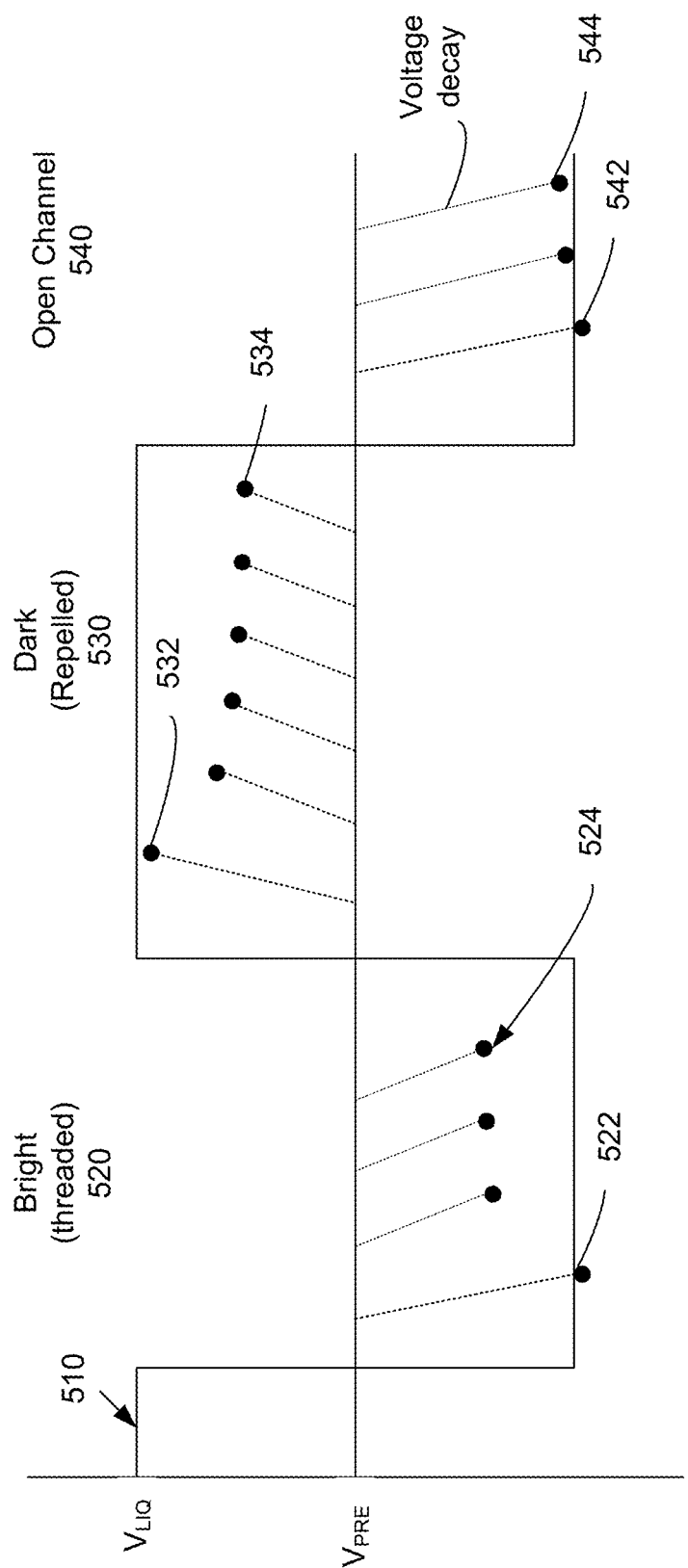
FIG. 5 shows example data points captured from a nanopore cell during bright periods and dark periods of AC cycles.

FIG. 5 shows example data points captured from a nanopore cell during bright periods and dark periods of AC cycles. In FIG. 5, the change in the data points is exaggerated for illustration purpose. The voltage ($V_{PRE}$) applied to the working electrode or the integrating capacitor is at a constant level, such as, for example, 900 mV. A voltage signal 510 ($V_{LIQ}$) applied to the counter electrode of the nanopore cells is an AC signal shown as a rectangular wave, where the duty cycle may be any suitable value, such as less than or equal to 50%, for example, about 40%.

During a bright period 520, voltage signal 510 ($V_{LIQ}$) applied to the counter electrode is lower than the voltage $V_{PRE}$ applied to the working electrode, such that a tag may be forced into the barrel of the nanopore by the electric field caused by the different voltage levels applied at the working electrode and the counter electrode (e.g., due to the charge on the tag and/or flow of the ions). When switch 401 is opened, the voltage at a node before the ADC (e.g., at an integrating capacitor) will decrease. After a voltage data point is captured (e.g., after a specified time period), switch 401 may be closed and the voltage at the measurement node will increase back to $V_{PRE}$ again. The process can repeat to measure multiple voltage data points. In this way, multiple data points may be captured during the bright period.

As shown in FIG. 5, a first data point 522 (also referred to as first point delta (FPD)) in the bright period after a change in the sign of the $V_{LIQ}$ signal may be lower than subsequent data points 524. This may be because there is no tag in the nanopore (open channel), and thus it has a low resistance and a high discharge rate. In some instances, first data point 522 may exceed the $V_{LIQ}$ level as shown in FIG. 5. This may be caused by the capacitance of the bilayer coupling the signal to the on-chip capacitor. Data points 524 may be captured after a threading event has occurred, i.e., a tag is forced into the barrel of the nanopore, where the resistance of the nanopore and thus the rate of discharging of the integrating capacitor depends on the particular type of tag that is forced into the barrel of the nanopore. Data points 524 may decrease slightly for each measurement due to charge built up at $C_{Double\ Layer}$ 424, as mentioned below.

During a dark period 530, voltage signal 510 ($V_{LIQ}$) applied to the counter electrode is higher than the voltage ($V_{PRE}$) applied to the working electrode, such that any tag would be pushed out of the barrel of the nanopore. When switch 401 is opened, the voltage at the measurement node increases because the voltage level of voltage signal 510 ($V_{LIQ}$) is higher than $V_{PRE}$. After a voltage data point is captured (e.g., after a specified time period), switch 401 may be closed and the voltage at the measurement node will decrease back to $V_{PRE}$ again. The process can repeat to measure multiple voltage data points. Thus, multiple data points may be captured during the dark period, including a first point delta 532 and subsequent data points 534. As described above, during the dark period, any nucleotide tag is pushed out of the nanopore, and thus minimal information about any nucleotide tag is obtained, besides for use in normalization. Therefore, the output voltage signals from the cells during the dark period may have little or no use.

FIG. 5 also shows that during bright period 540, even though voltage signal 510 ($V_{LIQ}$) applied to the counter electrode is lower than the voltage ($V_{PRE}$) applied to the working electrode, no threading event occurs (open-channel). Thus, the resistance of the nanopore is low, and the rate of discharging of the integrating capacitor is high. As a result, the captured data points, including a first data point 542 and subsequent data points 544, show low voltage levels.

The voltage measured during a bright or dark period might be expected to be about the same for each measurement of a constant resistance of the nanopore (e.g., made during a bright mode of a given AC cycle while one tag is in the nanopore), but this may not be the case when charge builds up at double layer capacitor 424 ($C_{Double\ Layer}$). This charge build-up can cause the time constant of the nanopore cell to become longer. As a result, the voltage level may be shifted, thereby causing the measured value to decrease for each data point in a cycle. Thus, within a cycle, the data points may change somewhat from data point to another data point, as shown in FIG. 5.

4. Determining Bases

For each usable nanopore cell of the nanopore sensor chip, a production mode can be run to sequence nucleic acids. The ADC output data captured during the sequencing can be normalized to provide greater accuracy. Normalization can account for offset effects, such as cycle shape and baseline shift. After normalization, embodiments can determine clusters of voltages for the threaded channels, where each cluster corresponds to a different tag species, and thus a different nucleotide. The clusters can be used to determine probabilities of a given voltage corresponding to a given nucleotide. As another example, the clusters can be used to determine cutoff voltages for discriminating between different nucleotides (bases).

Further details regarding the sequencing operation can be found in, for example, U.S. Patent Publication No. 2016/0178577 entitled "Nanopore-Based Sequencing With Varying Voltage Stimulus," U.S. Patent Publication No. 2016/0178554 entitled "Nanopore-Based Sequencing With Varying Voltage Stimulus," U.S. patent application Ser. No. 15/085,700 entitled "Non-Destructive Bilayer Monitoring Using Measurement Of Bilayer Response To Electrical Stimulus," and U.S. patent application Ser. No. 15/085,713 entitled "Electrical Enhancement Of Bilayer Formation."

III. Nanopore Cell Array

When the sequencing nanopore cells are arranged on the nanopore sensor chip, many nucleic acid molecules can be sequenced in parallel. Each cell can have some dedicated circuitry (e.g., an integrating capacitor), but also can share some circuitry, e.g., an ADC, a signal source, an electrode, or a control circuit.

Figure 6:
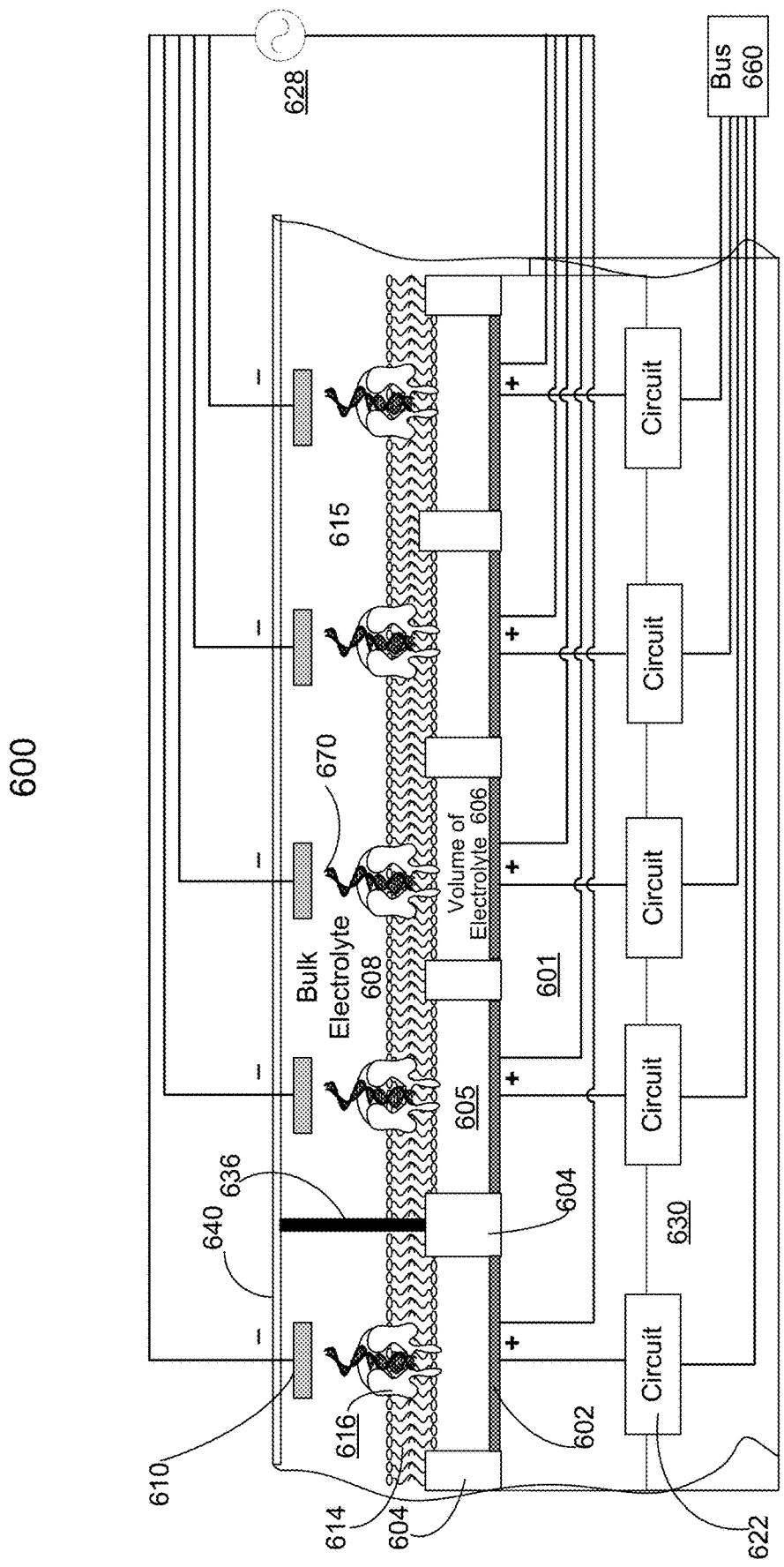
FIG. 6 is a cross-sectional view of an array of nanopore cells in an example nanopore sensor chip.

FIG. 6 is a cross-sectional view of an array 600 of nanopore cells in an example nanopore sensor chip, such as array of nanopore cells 150 in nanopore sensor chip 140 viewed along line A-A shown in FIG. 1. FIG. 6 shows a plurality of nanopore cells in a row or a column of array 600 of nanopore cells. As described above with respect to FIG. 2, each nanopore cell includes electric circuit 622 integrated on silicon substrate 630 and/or dielectric layer 601 of the nanopore sensor chip. Each nanopore cell includes a respective well 605 formed by dielectric layers 601 and 604 and working electrode 602 at the bottom of well 605. Well 605 can hold the volume of electrolyte 606. A lipid bilayer 614 can be formed on dielectric layer 604 and cover each well 605. Lipid bilayer 614 includes a nanopore 616 on top of each well 605. Sample chamber 615 on top of lipid bilayer 614 may be configured to hold bulk electrolyte 608, which may include the molecules to be analyzed, and polymer-tagged nucleotides, or primers as described above. A molecule 670 to be analyzed may be docked on nanopore 616, e.g., by an interaction between a polymerase and molecule 670). In some embodiments, side walls 636 (such as side walls 136 shown in FIG. 1) may be included in array 600 to separate groups of nanopore cell such that each group may receive a different sample for characterization. In some embodiments, the nanopore sensor chip may include cover plate 630 that encloses sample chamber 615.

Counter electrodes 610 from different nanopore cells may be disposed in sample chamber 615 and may be connected to voltage source 628 for applying a common $V_{LIQ}$ to the nanopore cells. Counter electrodes 610 for different nanopore cells may be physically connected to each other to form a common electrode. Working electrodes 602 of different nanopore cells may be connected to a common voltage source, or may be independently connected to different voltage sources. In some embodiments, electric circuits 622 of different nanopore cells may be connected to a bus 660, and the voltage level on the integrating capacitors of the different nanopore cells may be sequentially read out through bus 660 by sequentially selecting the different nanopore cells as described in detail below.

Figure 7:
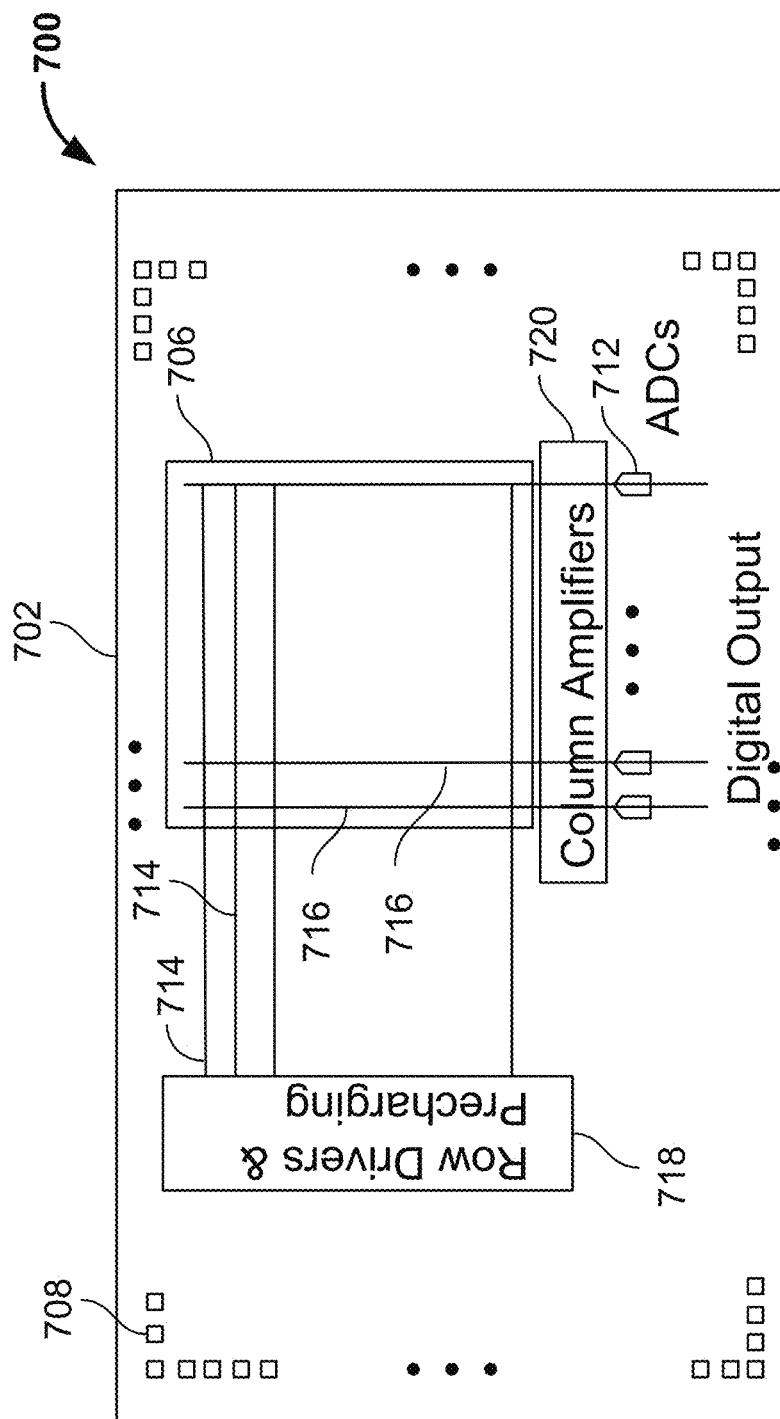
FIG. 7 is a top view of an example nanopore cell array including a two-dimensional array of nanopore cells.

FIG. 7 is a top view of an example nanopore cell array 700 including a two-dimensional array of nanopore cells 708. Nanopore cell array 700 may include thousands or even millions of nanopore cells. For example, in one embodiment, nanopore cell array 700 may include 512×512 nanopore cells arranged in 512 lines and 512 columns. In some embodiments, nanopore cell array 700 may be grouped into different banks 706, where each bank may include a subset of the nanopore cells in nanopore cell array 700. In some embodiments, nanopore cells in each column of nanopore cell array 700 may be grouped together, and the voltage levels at the integrating capacitors of the nanopore cells in each column may be sampled and converted by an ADC 712. The nanopore cells in a column may share a same ADC in order to reduce overall area and power consumption of the nanopore sensor chip.

Row drivers and pre-charging circuit 718 may be used to selectively pre-charge nanopore cells in one or more rows (e.g., by closing switch 401 of FIG. 4 to connect the nanopore cells in one or more rows to $V_{PRE}$ using row selection lines (or word lines) 714). Row drivers and pre-charging circuit 718 may also be used to sequentially select each row using row selection lines (i.e., word lines) 714. The integrating capacitors of the nanopore cells on the selected row may be connected to corresponding column lines 716 (e.g., through a switch (not shown) between on-chip integrating capacitor 408 ($n_{cap}$) and ADC 410, or through pass device 406 if on-chip integrating capacitor 408 ($n_{cap}$) is not used). The voltage signals from the nanopore cells on the selected row may be optionally processed (e.g., sensed and amplified) by corresponding column amplifiers 720, and converted to digital outputs by corresponding ADCs 712. In some embodiments, multiple columns could be served by the same column amplifier and ADC.

Figure 8:
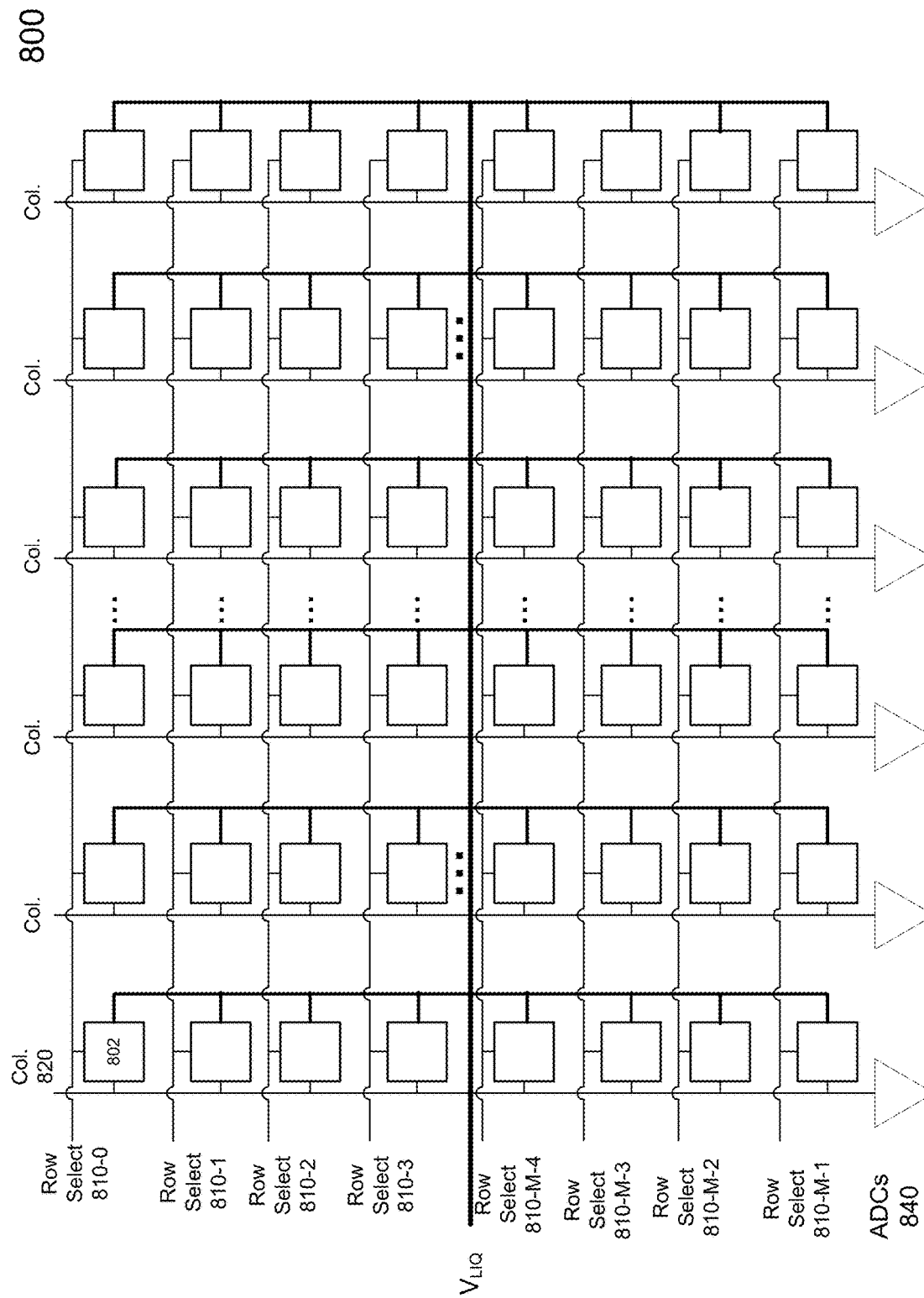
FIG. 8 is a schematic of an example nanopore cell array including a two-dimensional array of nanopore cells.

FIG. 8 is a schematic of an example nanopore cell array 800 including a two-dimensional array of nanopore cells 802. Nanopore cell array 800 may include all nanopore cells of a nanopore sensor chip, or may only include a subset (e.g., a bank) of the nanopore cells of a nanopore sensor chip. The working electrode of each nanopore cell 802 may be connected to a voltage source (e.g., $V_{PRE}$ of FIG. 4) (not shown), and the counter electrode of each nanopore cell 802 may be connected to a common signal $V_{LIQ}$. Nanopore cell array 800 includes a plurality of column lines 820, each column line 820 coupled to nanopore cells 802 in a same column and coupled to an ADC 840. Nanopore cell array 800 includes M rows of nanopore cells 802, where each of the M rows is selectable by row select lines 810-0 to 810-M-1.

During the sequencing process, an integrating capacitor of each nanopore cell 802 may first be pre-charged by a voltage source $V_{PRE}$ applied to the working electrode (e.g., through switch 401 as shown in FIG. 4), and the common signal $V_{LIQ}$ may be applied to the counter electrodes of nanopore cells 802, as described above. After the integrating capacitors on nanopore cells 802 have been charged/discharged, each of the M rows may be selected sequentially to connect the integrating capacitors of the nanopore cells on a row to the corresponding column lines and corresponding ADCs. The integrating capacitors may be buffered to prevent coupling through parasitic capacitors. ADC 840 for a column may thus sequentially sample and convert the voltage levels of the integrating capacitors of the nanopore cells in the column.

In this way, one set of data samples may be captured from the nanopore cells in a column of a nanopore cell array after each pre-charging and charging/discharging operation. When multiple pre-charging and charging/discharging operations are performed in the bright and dark periods of an AC cycle, multiple sets of data samples may be captured, where each set of data samples includes one data sample from each of the nanopore cells in the column.

Figure 9:
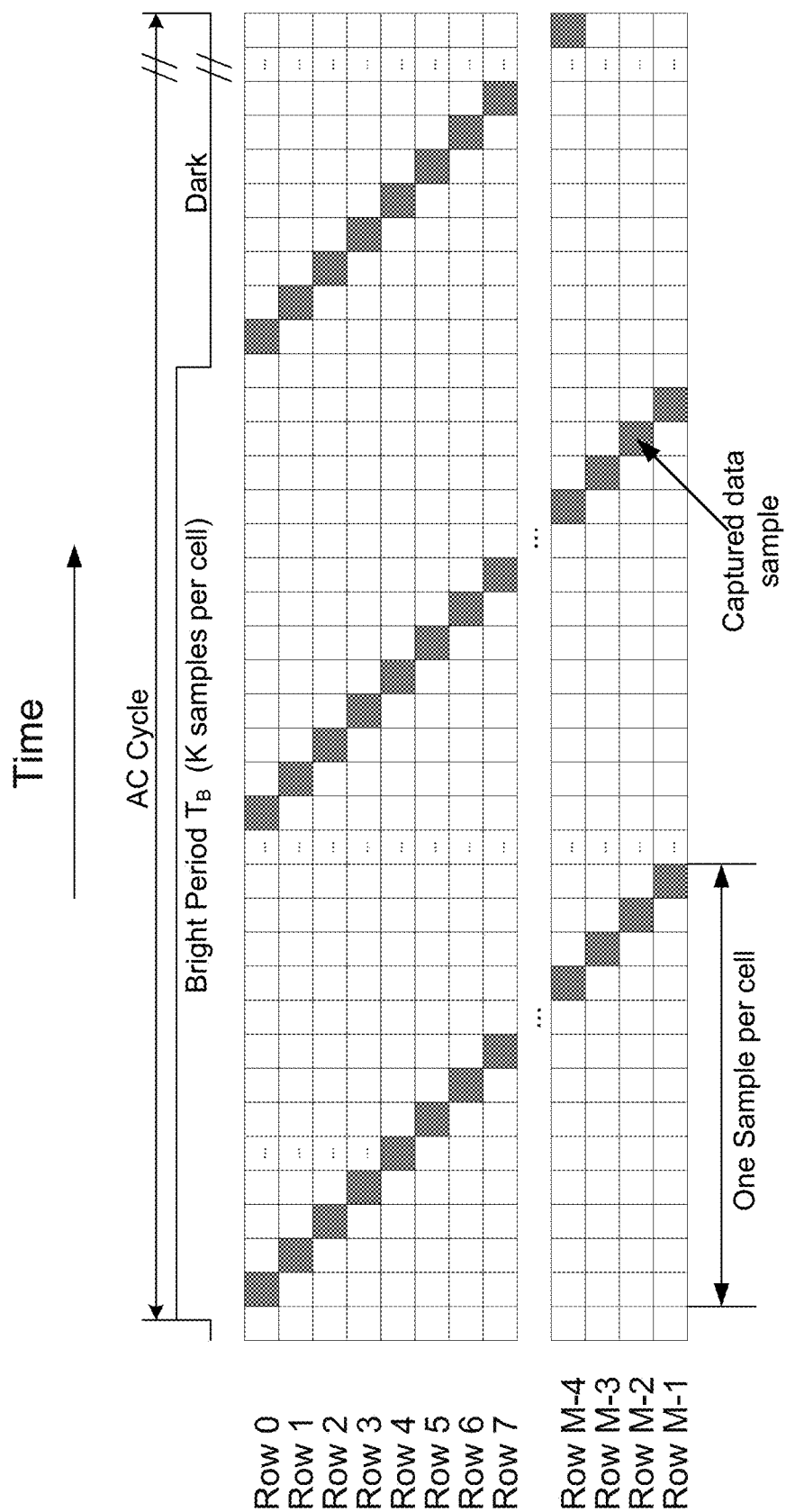
FIG. 9 illustrates example data samples captured from nanopore cells in a column of a nanopore cell array.

FIG. 9 illustrates example data samples captured from nanopore cells in a column of a nanopore cell array, such as nanopore cell array 800, during an AC cycle. In FIG. 9, the horizontal axis represents the time during the sequencing process. FIG. 9 shows that, during the time $T_B$ of a bright period of an AC cycle, a total of K samples may be captured from each nanopore cell by an ADC serving the column.

As described above with respect to FIG. 8, a column of the nanopore cell array may include M nanopore cells, each on a different row. The ADC may capture one data sample for the nanopore cell in row 0, one data sample for the nanopore cell in row 1, . . . , and one data sample for the nanopore cell in row M−1. Each ADC capture can be controlled by a clock signal that is much faster than the AC signal applied to the electrodes of the nanopore cells. After each nanopore cell in the column has been sampled once, the nanopore cell in the column may again be pre-charged by the voltage source $V_{PRE}$, and charged/discharged by the common signal $V_{LIQ}$. Afterwards, a second data sample may be captured from each of the M nanopore cells in the column sequentially or in a pipeline. The sequencing process may be repeated to capture K samples from each of the M nanopore cells in the column during the bright period. As a result, a total number of M×K samples may be captured from the M nanopore cells in each column during the time $T_B$ of the bright period. Thus, the sample rate of the ADC may be at least $M \times K/T_B$ in order to capture M×K samples during the time $T_B$ of the bright period. Data samples can be captured in a similar manner during the dark period.

IV. Phased Nanopore Cell Arrays

As discussed above, there is an upper limit to the possible sampling rate due to, for example, limited sampling and conversion speed of analog-to-digital converters, and/or limited bandwidth of buses, data storage devices, or data processing circuits. When all nanopore cells in a column are controlled by a common $V_{LIQ}$ signal, almost all useful data is captured during the common bright period, while during the dark period, little or no useful data may be captured. Thus, a significant portion of the bandwidth of a data sampling and conversion circuit may not be utilized to capture useful data at least during the dark period.

Techniques disclosed herein address the above issues and increase the effective sampling rate per cell of the sampling and conversion circuit by applying AC signals with different phases to different nanopore cells in a column. As a result, when some nanopore cells are in the dark period, some other nanopore cells are in the bright period and being sampled by the shared sampling and conversion circuit. For example, in some embodiments, the nanopore cells in a column may be organized into two or more groups. A common $V_{LIQ}$ may be applied to the counter electrodes of all nanopore cells, and the phase of an AC signal $V_{PRE}$ applied to the working electrodes of nanopore cells in each group of nanopore cells may be delayed by a different value. In this way, at any given time, the data sampling and conversion circuit may sample and convert the output voltage signals from the portion of the nanopore cells in a column that are in the bright period, with the dark period being sampled minimally, e.g., for normalization purposes only. As such, the data sampling and conversion can be performed at a higher rate for each nanopore cell in the bright period. Furthermore, because the dark period is only sampled minimally, all or almost all of the data captured would be useful, as opposed to the instance where the dark period is being sampled at an unnecessarily high rate.

A. Architecture

Figure 10:
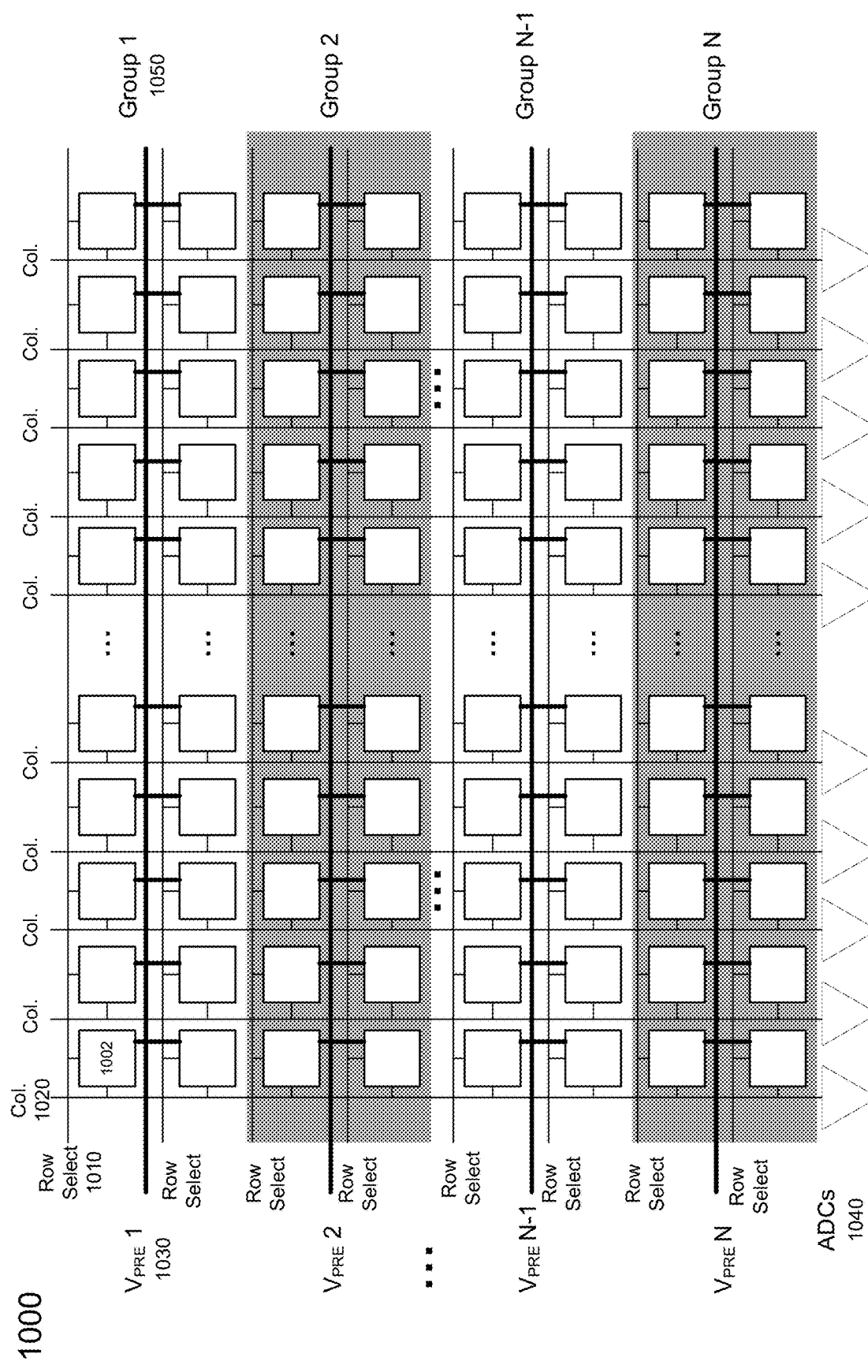
FIG. 10 is a schematic of an example nanopore cell array including a two-dimensional array of nanopore cells, according to certain aspects of the present disclosure.

FIG. 10 is a schematic of an example nanopore cell array 1000 including a two-dimensional array of nanopore cells 1002, according to certain aspects of the present disclosure. Similar to nanopore cell array 800 of FIG. 8, nanopore cell array 1000 may include all nanopore cells of a nanopore sensor chip, or may only include a subset of the nanopore cells of a nanopore sensor chip. Nanopore cell array 1000 includes a plurality of column lines 1020, each column line 1020 coupled to nanopore cells 1002 in a same column and coupled to an ADC 1040. Nanopore cell array 1000 includes M rows of nanopore cells 1002, where each of the M rows is selectable by a row select line 1010. Nanopore cells 1002 in nanopore cell array 1000 may be organized into N groups, where N may be any number between 2 and the total number of nanopore cells in the column. In one embodiment, nanopore cell array 1000 may be organized such that each group of the N groups may include the nanopore cells in M/N rows. In other embodiments, the nanopore cells 1002 in nanopore cell array 1000 may be organized into N groups in a different manner. For example, some groups may have more nanopore cells than some other groups. In some embodiments, nanopore cells in every other row may be in a same group. In some embodiments, nanopore cells in alternate pairs of rows may be in a same group. In some embodiments, nanopore cells in a group may be in a same region. In some embodiments, nanopore cells in a group may not be in a same region and may be separated by nanopore cells in other groups.

Figure 11:
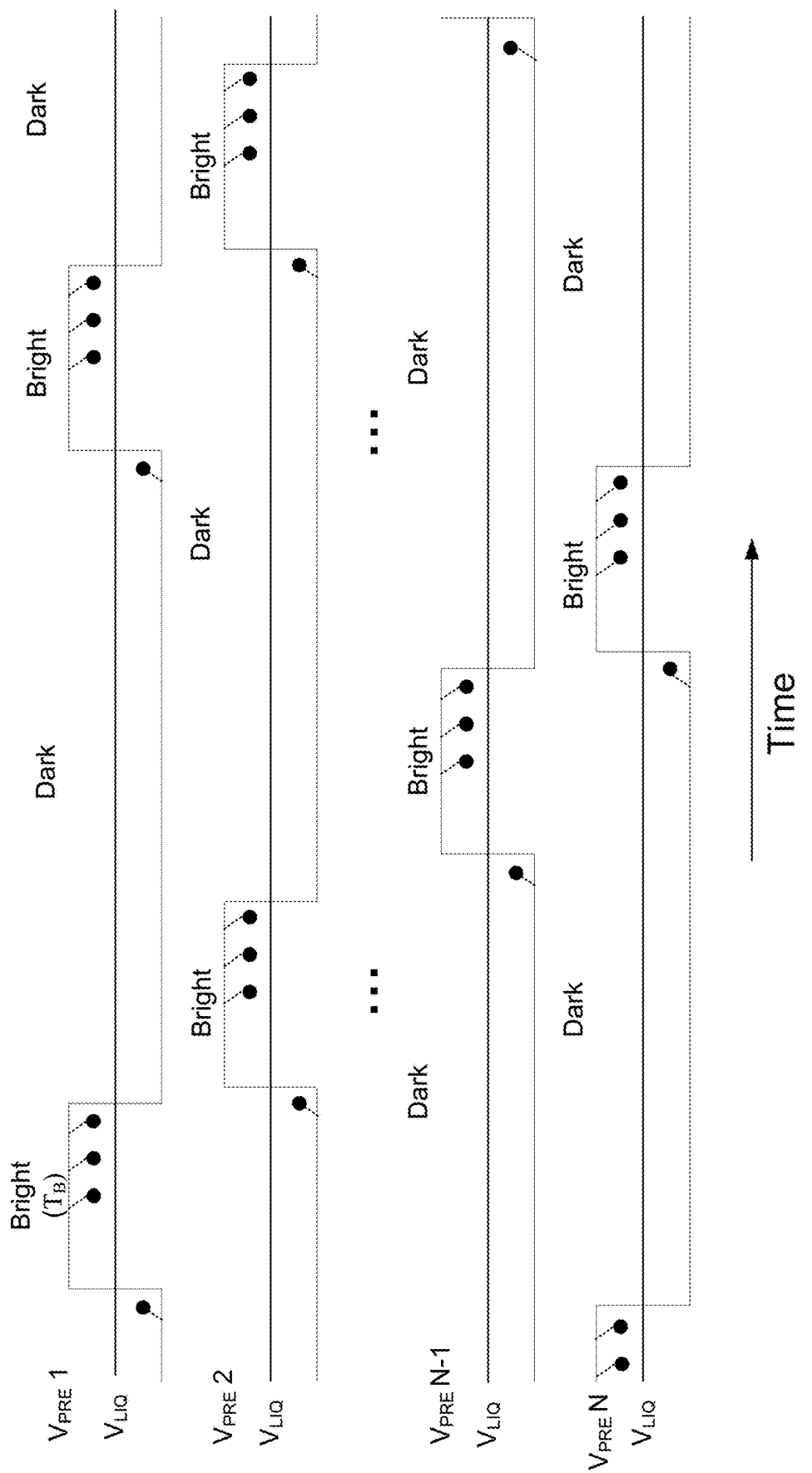
FIG. 11 illustrates example control signals for a nanopore cell array, according to certain aspects of the present disclosure.

The counter electrode of each nanopore cell 1002 in nanopore cell array 1000 may be connected to a common signal $V_{LIQ}$ (not shown), which may be a constant voltage level. The working electrodes of the nanopore cells 1002 in each group of the N groups may be connected to a common signal $V_{PRE}$ (1030), where the signals $V_{PRE}$ for the N groups (i.e., $V_{PRE}1, V_{PRE}2, V_{PRE}N$) may be independently applied to the N groups and may be at different phases from each other. For example, the signals $V_{PRE}$ for the N groups may be from a same signal source but may be delayed differently by delay lines or gates. The delay allows the sampling to be primarily for the bright period, as illustrated in FIG. 11 below. In this way, control at a higher granularity can be achieved with more groups of nanopore cells receiving different $V_{PRE}$ signals. Because the grouping is done electrically by applying a same $V_{PRE}$ signal to nanopore cells in a group, the grouping may be scalable and dynamically configurable when the working electrodes of the nanopore cells are independently addressable at a subgroup level or at a cell level.

In some implementations, each nanopore cell may include a switch. The switch may be connected to switch 401 of FIG. 4, e.g., upstream of switch 401 or in parallel with switch 401, but with a coordinated control signal. The switch may selectively connect the working electrode of the nanopore cell (and voltage signal $V_{PRE}$ 405) to a high voltage level or a low voltage level. For example, the switch may be controlled by an AC control signal, such as a square wave or a rectangular wave signal, such that the working electrode may be connected to the high voltage level during a portion of a cycle of the AC control signal, and may be connected to the low voltage level during another portion of the cycle. In some embodiments, the switch may be implemented using two switches controlled by inverse control signals, where one switch may be configured to connect the working electrode to the high voltage level and the other switch may be configured to connect the working electrode to the low voltage level. The AC control signal may be a digital signal, such as a digital clock signal. The high voltage level may be higher than common signal $V_{LIQ}$, and the low voltage level may be lower that common signal $V_{LIQ}$. As such, an AC $V_{PRE}$ signal may be effectively applied to the nanopore cell. Different $V_{PRE}$ signals may be applied to different nanopore cells by applying different digital AC control signals (e.g., with different phase delays) to the nanopore cells. Some nanopore cells may receive digital AC control signals with the same phase to form a group of the N groups of nanopore cells. In this way, a group may include one or more nanopore cells, and the grouping of the nanopore cells can be more flexible and dynamic. For example, the grouping can be changed dynamically by changing the digital AC control signals applied to the nanopore cells, and nanopore cells that are not in a same vicinity may form a group.

In some implementations, the nanopore sensor chip may include two or more different fluidic channels above the nanopore cells of the nanopore sensor chip. The nanopore cells in the nanopore sensor chip may be grouped based on the fluidic channels that they are in. For example, nanopore cells in different fluidic channels may be assigned to different groups. In some implementations, nanopore cells in two or more fluidic channels may be grouped together. A different AC signal $V_{LIQ}$ may then be used to drive the counter electrodes of nanopore cells in a different group. For example, the AC signals for driving the counter electrodes of nanopore cells in different groups may have different phases or delays. As a results of the different phases of the $V_{LIQ}$ signals, nanopore cells in different groups may be in the bright period at different times, and thus the outputs of the nanopore cells in different groups can be sampled at different times by a shared sampling circuit.

B. AC Signals of Different Cell Groups Having Different Phases

FIG. 11 illustrates example AC signals ($V_{PRE}$) for a nanopore cell array, such as nanopore cell array 1000, according to certain aspects of the present disclosure. The nanopore cells in nanopore cell array 1000 having M rows may be organized into N groups. FIG. 11 includes a plurality of graphs, each graph showing the AC signal applied to a group of cells of the N groups and the corresponding sample points. The horizontal axis in FIG. 11 represents the time during the sequencing process.

As shown in FIG. 11, the counter electrode of each nanopore cell in nanopore cell array 1000 may be connected to a common signal $V_{LIQ}$, which may be a constant voltage level. The working electrodes of the nanopore cells in each group of the N groups may be connected to a signal $V_{PRE}$, where the signals $V_{PRE}$ for the N groups (i.e., $V_{PRE}1, V_{PRE}2, \ldots, V_{PRE}N$) may be at different phases from each other.

In some embodiments, the signals $V_{PRE}$ for the N groups may each be delayed incrementally from others by a time period approximately equal to the bright period. In the example shown in FIG. 11, the N $V_{PRE}$ signals are rectangular AC signals that toggle between a high voltage level and a low voltage level. The $V_{PRE}$ signals are delayed from each other such that, when nanopore cells in one group are in the bright period (e.g., when $V_{LIQ}$ is lower than $V_{PRE}$), nanopore cells in other groups are in the dark period.

For example, for nanopore cells in group 1, during the bright period, signal $V_{PRE}1$ may be at the high voltage level that may be higher than the constant $V_{LIQ}$, and the integrating capacitor in each nanopore cell in group 1 that is controlled by $V_{PRE}1$ may first be pre-charged to the high voltage level of $V_{PRE}1$. The integrating capacitor may then be disconnected from $V_{PRE}1$, and be discharged by the low level signal $V_{LIQ}$ through the nanopore. The rate of discharge depends on the resistance of the nanopore, which may vary when tags of different structures and sizes are forced into the barrel of the nanopore as described above. The voltage level of the integrating capacitor may be measured by the sampling and conversion circuit (e.g., an ADC) after the integrating capacitor has been discharged for a selected time period. One or more samples may be captured from a nanopore cell in this manner during the bright period.

When nanopore cells in group 1 controlled by $V_{PRE}1$ are in a bright period of width $T_B$, nanopore cells in groups 2-N controlled by signals $V_{PRE}2$ to $V_{PRE}N$, respectively, may be in a dark period. During this time period $T_B$, M/N, rather than M, nanopore cells in a column may be served by one ADC. Thus, to capture K samples for each nanopore cell during time period $T_B$, an ADC with a sampling rate of $(M \times K/T_B)/N$ may be used. In other words, an ADC with a sampling rate of $M \times K/T_B$ may be able to capture $K \times N$ (rather than K) samples for each nanopore cell during time period $T_B$. Accordingly, each nanopore cell may be sampled at a faster rate (e.g., N times as fast) and thus may detect events having shorter durations.

After signal $V_{PRE}$ 1 toggles to the low voltage level, nanopore cells in group 1 may enter the dark period. During the dark period, signal $V_{PRE}$ 1 may be at the low voltage level that may be lower than the constant $V_{LIQ}$ level, and the tags associated with the nucleotides may be pushed out of the nanopores. In various embodiments, no data sample may be captured during the dark period or, one or more data samples at the end (or beginning) of the dark period may be captured in each AC cycle, for example, for normalization purposes. To further limit sampling in a dark period, only some dark periods may be sampled, e.g., every nth dark period, such as every $8^{th}$ dark period. To capture a data sample in the dark period, the integrating capacitor in each nanopore cell in group 1 that is controlled by $V_{PRE}$ 1 may first be pre-charged to the low voltage level of $V_{PRE}$ 1. The integrating capacitor may then be disconnected from $V_{PRE}$ 1, and be charged by signal $V_{LIQ}$ through the nanopore. The charge rate depends on the resistance of the nanopore as described above.

After signal $V_{PRE}$ 1 toggles to the low voltage level, signal $V_{PRE}$ 2 may toggle from the low voltage level to the high voltage level such that nanopore cells in group 2 that are controlled by signal $V_{PRE}$ 2 may enter the bright period, and data samples from the nanopore cells in group 2 may be captured by the shared sampling and conversion circuit. As described above, multiple data samples may be captured for each nanopore cell in group 2 during the bright period, and one or more data samples from each nanopore cell in group 2 may be captured at the end of a dark period during one or more AC cycles for normalization purposes.

Nanopore cells in each of groups 3 to N may enter the bright period sequentially, and multiple data samples from each of the nanopore cells in each group may be captured by the shared sampling and conversion circuit in the manner described above. After nanopore cells from group N enter the dark period from the bright period, nanopore cells from group 1 may again enter the bright period in a new AC cycle for sequencing data sampling.

Figure 12:
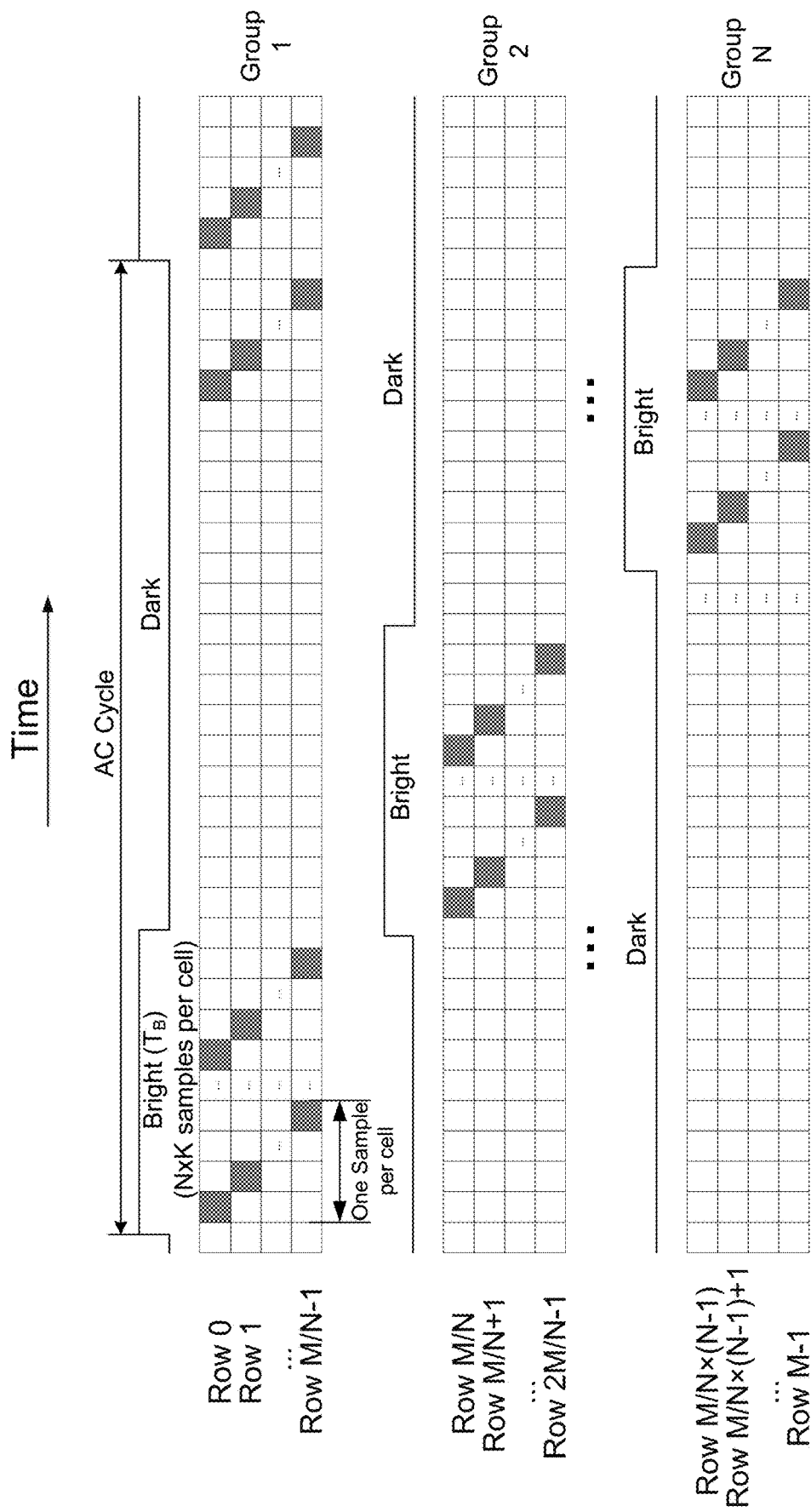
FIG. 12 illustrates example data samples captured from nanopore cells in a column of a nanopore cell array, according to certain aspects of the present disclosure.

FIG. 12 illustrates example data samples captured from nanopore cells in a column of a nanopore cell array, such as nanopore cell array 1000, according to certain aspects of the present disclosure. The horizontal axis in FIG. 12 represents the time during the sequencing process. Grey boxes in the diagram indicate row selection events. The column of the nanopore cell array includes M nanopore cells, each on a different row. The M nanopore cells are organized in N different groups, with MN nanopore cells in each group. When nanopore cells in group 1 (nanopore cells in rows 0 to M/N−1) subject to $V_{PRE}$ 1 are in the bright period $T_B$, nanopore cells in groups 2 to N controlled by signals $V_{PRE}$ 2 to $V_{PRE}$ N, respectively, may be in the dark period. Therefore, during the bright period $T_B$, only outputs from nanopore cells in row 0 to M/N−1 may be captured by the ADC serving the column.

Each of the nanopore cells in group 1 may be pre-charged to the high level of signal $V_{PRE}$ 1, and discharged by signal $V_{LIQ}$ through the nanopore. After a selected discharge time, the ADC may capture one data sample for the nanopore cell in row 0, one data sample for the nanopore cell in row 1, . . . , and one data sample for the nanopore cell in row M/N−1. After each cell in the column that belongs to group 1 has been sampled once, each of the nanopore cells in group 1 may again be pre-charged to the high level of signal $V_{PRE}$ 1, and discharged by signal $V_{LIQ}$ through the nanopore. After the selected discharge time, the ADC may capture a second data sample for the nanopore cell in row 0, a second data sample for the nanopore cell in row 1, . . . , and a second data sample for the nanopore cell in row M/N−1. The sequencing process may be repeated to capture multiple samples from each of the M/N nanopore cells in group 1 during the bright period. Thus, for an ADC with a sample rate of $M \times K/T_B$, a total number of $N \times K$ samples may be captured from each of the M/N cells in group 1 during the bright period $T_B$, as compared with K samples captured from each of nanopore cell during the bright period $T_B$ illustrated in FIG. 9. Thus, compared with the nanopore cells in nanopore cell array 800, each nanopore cell in nanopore cell array 1000 can be measured N times as fast without using a faster sampling and conversion circuit, and can thus detect events having shorter durations.

Similarly, when nanopore cells in group 2 (or any of groups 3 to N) are in the bright period and nanopore cells in other groups are in the dark period, a total number of $N \times K$ samples may be captured from each of the M/N cells in group 2 (or any of groups 3 to N) during the bright period $T_B$.

In this way, the data sampling and conversion circuit can sample and convert output signals from each nanopore cell in the portion of the nanopore cells at a higher sampling rate by only serving a portion of the nanopore cells in a column at a given time, even if the overall speed of the data sampling and conversion circuit is not changed. Therefore, events having shorter durations may be detected.

Additionally or alternatively, the frequency of the AC control signal (e.g., $V_{PRE}$) may be increased with or without increasing the number of samples captured during the bright period. As a result, sequencing a polymer molecule with a certain number of units (e.g., bases) may take a shorter period of time because of the shorter AC cycle. In addition, because the effective sampling rate is higher for each nanopore cell with the shorter AC cycle, events having shorter durations may be detected.

FIGS. 11 and 12 illustrate embodiments where there may be no overlapping among the bright periods of different $V_{PRE}$ signals for different groups of nanopore cells. Such embodiments may occur when the bright period of each AC control signal is shorter than the period of the AC cycle divided by the number of groups N, i.e., the duty cycle of the AC control signal is no greater than 1/N. For example, when the nanopore cells in the nanopore cell array are organized into two groups, and the duty cycle of the AC control signal is no greater 50%, i.e., the bright period is equal to or shorter than the dark period, no overlapping between the bright periods of the $V_{PRE}$ signals for the two groups of nanopore cells may occur. Although the $V_{PRE}$ signals for different groups in FIGS. 11 and 12 are shown to have some similar properties (e.g., the same voltage levels, duty cycle, and cycle time) and may be derived from a same signal source by different delays, the $V_{PRE}$ signals for different groups may be independent from each other, because the working electrode of each nanopore cell may be independent from the working electrodes of other nanopore cells. Thus, the $V_{PRE}$ signals may have different voltage levels, duty cycles, cycle times, and phases.

As described above, in some implementations, each nanopore cell may include a switch, which may be controlled by an AC control signal to alternately connect the working electrode of the nanopore cell (and $V_{PRE}$) to a high voltage level and a low voltage level. The high voltage level may be higher than the common signal $V_{LIQ}$, and the low voltage level may be lower than the common signal $V_{LIQ}$. Thus, $V_{PRE}$ signals with different phases may be effectively applied to the working electrodes of different groups of nanopore cells or different individual nanopore cells using digital AC control signals with different phases for the switches.

As described above, in some implementations, the nanopore cells in the nanopore sensor chip may be grouped based on the fluidic channels that they are in, and a different AC signal $V_{LIQ}$ may be used to drive the counter electrodes of nanopore cells in a different group, rather than using a different AC signal $V_{PRE}$ for each group as described with respect to FIG. 11. In such implementations, the $V_{LIQ}$ signals for different groups may be delayed differently, similar to the way the $V_{PRE}$ signals are configured in FIG. 11. The outputs of the nanopore cells in different groups can be sampled at different times by a shared sampling circuit (e.g., ADC) in a way similar to the way the nanopore cells are sampled as described with respect to FIG. 12.

C. Adaptive and Selective Sampling

In some implementations, the $V_{PRE}$ signals may be configured such that there may be an overlapping period among the bright periods of different $V_{PRE}$ signals applied to different groups of nanopore cells. In such implementations, the data sampling and conversion circuit or a control circuit may be configured to determine output voltage signals from which group of nanopore cells are to be sampled and converted during each overlapping period in different AC cycles.

Figure 13:
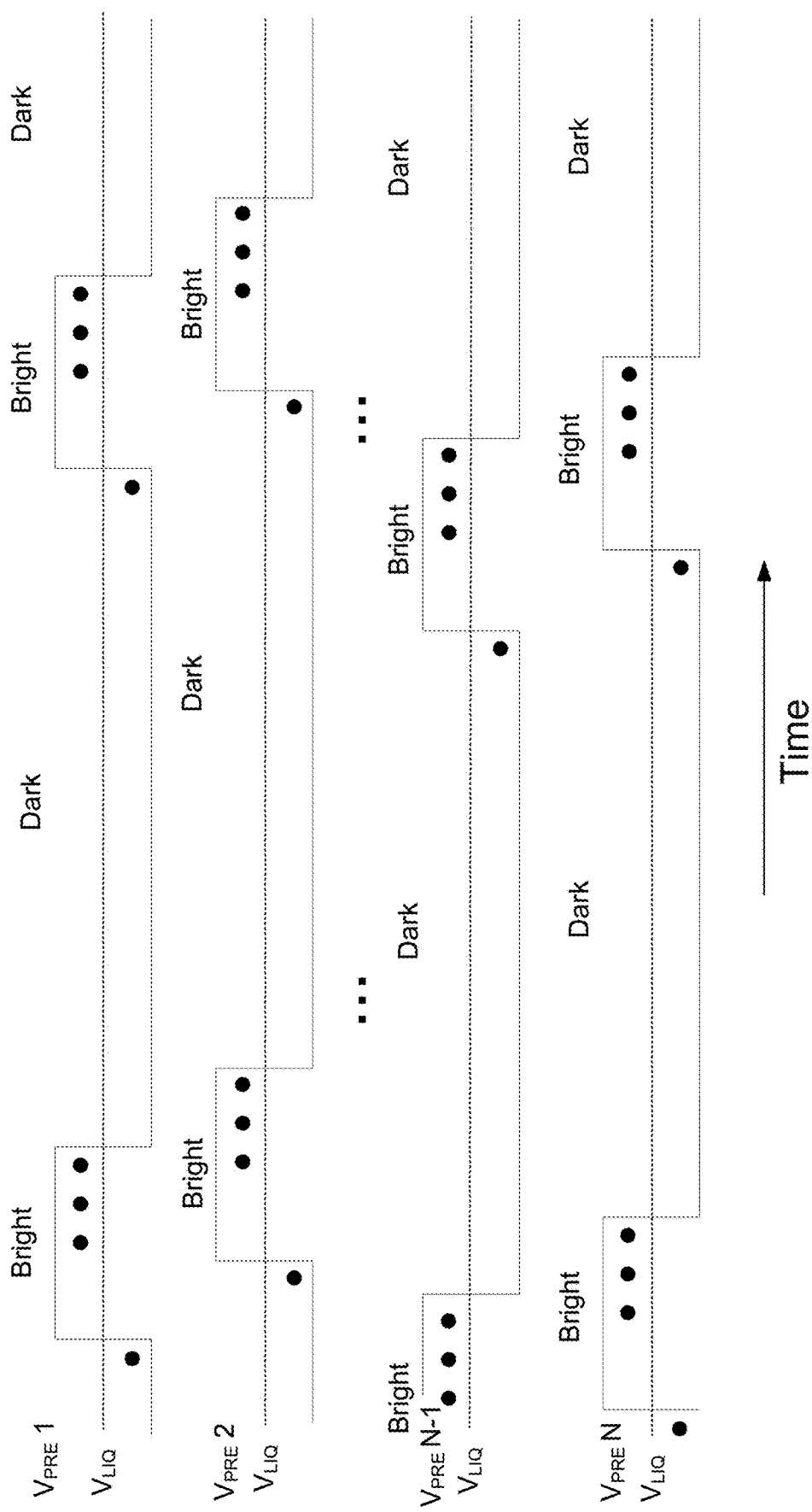
FIG. 13 shows example control signals for a nanopore cell array, according to certain aspects of the present disclosure.

FIG. 13 shows example control signals ($V_{PRE}$) for a nanopore cell array, such as nanopore cell array 1000, according to certain aspects of the present disclosure. The horizontal axis in FIG. 13 represents the time during the sequencing process. As shown in FIG. 13, the counter electrode of each nanopore cell in nanopore cell array 1000 may be connected to a common signal $V_{LIQ}$, which may be a constant voltage level. The working electrodes of the nanopore cells in each group of the N groups may be connected to a signal $V_{PRE}$, where the signals $V_{PRE}$ for the N groups (i.e., $V_{PRE}$ 1, $V_{PRE}$ 2, ..., $V_{PRE}$ N) are at different phases from each other. For example, where the duty cycle of the signals $V_{PRE}$ is greater than 1/N, one or more of the signals $V_{PRE}$ for the N groups may each be delayed incrementally from others by a time period shorter than the bright period. As a result, there may be an overlapping period among the bright periods of different $V_{PRE}$ signals applied to different groups of nanopore cells. An advantage of such implementation is that duty cycles with higher than 50% bright period can be used, or the cells can be divided into more than two groups and be controlled by more than two signals with different phases.

During the non-overlapping bright period, each nanopore cell in a group of nanopore cell array 1000 that is in the bright period may be sampled at a higher rate (as described above with respect to FIGS. 11 and 12) than the nanopore cell shown in FIG. 8. In some cases, during the overlapping period, the data sampling and conversion circuit or a control circuit may dynamically determine the group(s) of nanopore cells to be sampled, while ignoring the output signals from other group(s) of nanopore cells that are in the overlapping bright period. In some cases, during the overlapping interval, the sampling rate of the nanopore cells in different groups in the bright period may be reduced since nanopore cells from more than one group are in the bright period. For example, in some cases, the sampling rate of the nanopore cells in different groups in the bright period may be at an equal but reduced rate relative to the sampling rate when only one group is in a bright period. In other cases, the sampling rate of the nanopore cells in different groups in the bright period may be at reduced and different rates.

D. Advantages

Techniques described in the present disclosure enable controlling the nanopore cells at a higher granularity, such as at an individual cell level or at a group level, rather than applying a common control signal to all nanopore cells. As such, the number of cells in the bright period may be more constant over time, and the sampling and conversion rate for each cell in the bright period may be increased without changing the overall speed of the data sampling and conversion circuit, because the available resources are more efficiently utilized at any given time.

In addition to increasing the effective sampling rate for each nanopore cell to detect events having short durations and reducing the sequencing time as described above, other advantages may be achieved using techniques disclosed herein. For example, the bandwidth of the data sampling and conversion circuit may be fully utilized at any given time to capture data samples that are useful for sequencing. Thus, a nanopore sensor chip with a higher density or a higher number of cells may become possible. Additionally or alternatively, with reduced data sampled captured from cells in the dark period, the amount of data to be transported from the nanopore sensor chip and processed by subsequent storage or processing circuits may be reduced, which may reduce the cost of the sequencing system because circuits with lower performance (e.g., speed or bandwidth) or capacity (e.g., memory space or data channels) may be used.

Further, because some nanopore cells are in the dark period while some other nanopore cells are in the bright period during the same time and because a common $V_{LIQ}$ is applied to (shared by) the counter electrodes of all cells, the total current on the counter electrode may be at least partially reduced at any given time. This is caused by the opposite polarities of the current from the cells in the dark period and the current from the cells in the bright period, where electrons flowing into the counter electrode and electrons flowing out of the electrode may cause the net current on the counter electrode to be reduced. Furthermore, because of the AC nature of the $V_{PRE}$ signal, the current on the counter electrode and working electrode for each cell may also be balanced over time.

In some implementations, rather than being a constant voltage level, the $V_{LIQ}$ signal applied to the counter electrodes may also be an AC signal, but at a lower frequency than the $V_{PRE}$ signal applied to the working electrodes. In this way, even if there is any imbalance between the current from the cells in the dark period and the current from the cells in the bright period (e.g., because the duty cycle is different from 50% and a number of groups of nanopore cells in the dark period may be different from a number of groups of nanopore cells in the bright period) at a given time, the overall current on the counter electrode may be balanced over time. As such, the voltage drop on the counter electrode and thus the shifting of the output voltage may be reduced.

V. ADC Input Range Control

In many instances, the voltage levels on the integrating capacitor (e.g., integrating capacitor 408 ($n_{cap}$)) to be measured may cluster within certain smaller ranges. Thus, an ADC's dynamic range may not be fully utilized if the input range of the ADC is fixed. To fully utilize the dynamic range of the ADC, the input range of the ADC may be dynamically changed by adaptively changing the reference levels of the ADC based on the estimated voltage level to be measured.

In an ADC, the full-scale input range and the common mode voltage of the ADC may depend on the reference levels of the ADC, such as the positive reference level ($V_{REFP}$) and the negative reference level ($V_{REFN}$). The common mode voltage may be the average of $V_{REFP}$ and $V_{REFN}$. When a signal to be sampled by the ADC is at a voltage level close to $V_{REFN}$, the input of the ADC may be close to a zero scale, that is, the output of the ADC may represent a value close to the lowest possible value; The exact output code may depend on the coding scheme of the ADC, which may include, for example, straight binary, offset binary, two's complement, etc.

When a signal to be sampled by the ADC is at a voltage level close to $V_{REFP}$, the input of the ADC may be close to a full scale, and the output of the ADC may represent a value close to the highest possible value. To fully utilize the dynamic range of the ADC (i.e., the range of signal amplitudes which the ADC can resolve), it is desirable that the input signal level is more fully distributed between $V_{REFP}$ and $V_{REFN}$, rather than clustered within certain smaller ranges. For an 8-bit ADC, if the input signal level is between 0 V and 1 V, $V_{REFP}$ may be set to 1 V and $V_{REFN}$ may be set to 0 V; and the ADC may be able to differentiate two signal levels with a difference greater than about 4 mV. If the input signal level is between 0.25 V and 0.5 V, $V_{REFP}$ may be set to 0.5 V and $V_{REFN}$ may be set to 0.25 V; and the ADC may be able to differentiate two signal levels with a difference greater than about 1 mV.

However, as shown in FIG. 11 or 13, in some cases, the voltage levels of the integrating capacitors to be sampled by the ADC may not be distributed in the full range between the low voltage level and the high voltage level of the $V_{PRE}$ signals. Thus, with fixed reference levels ($V_{REFP}$ and $V_{REFN}$) of the ADC, the dynamic range of the ADC may not be fully utilized as the output codes may only include a portion of all possible codes (e.g., 256 different codes for an 8 bit ADC), or in other words, the signal levels may not be resolved with the maximum possible resolution of the ADC.

Figure 14A:
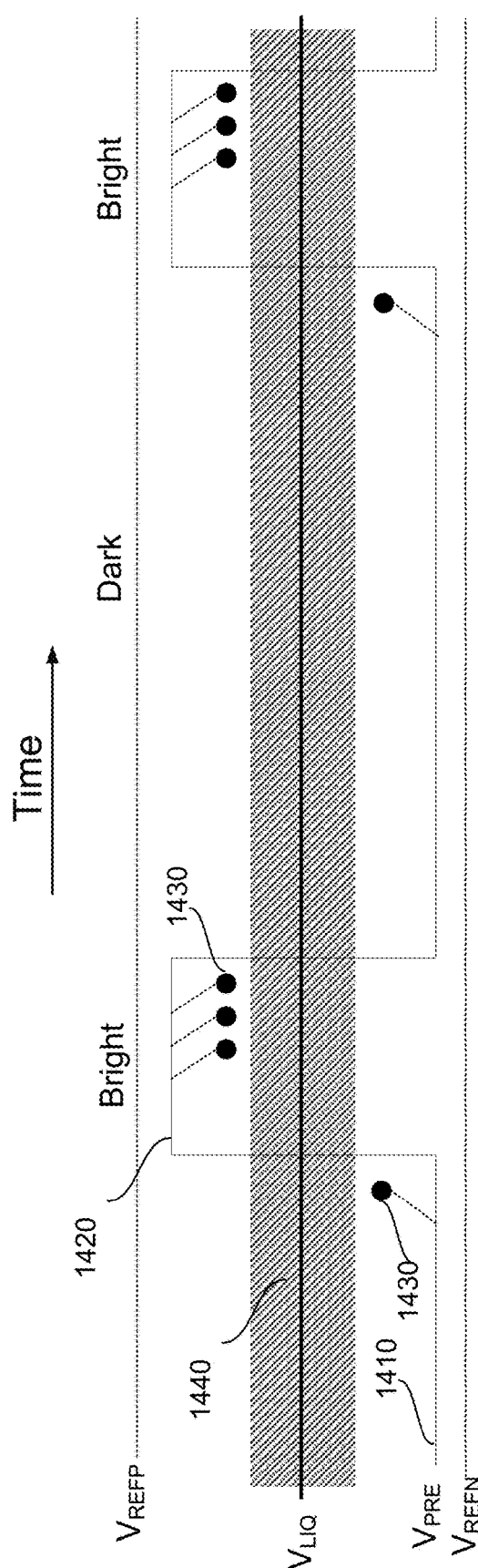
FIG. 14A shows fixed reference levels for an ADC in a nanopore sensor chip, according to certain aspects of the present disclosure.

FIG. 14A shows fixed reference levels for an ADC in a nanopore sensor chip. As shown in FIG. 14A, the voltage levels 1430 of the integrating capacitors to be sampled by the ADC may be close to the low voltage level 1410 of $V_{PRE}$ or the high voltage level 1420 of $V_{PRE}$. Thus, in order to include all these voltage levels in the input range of the ADC, $V_{REFP}$ for the ADC may be set at a level slightly above the high voltage level 1420 of $V_{PRE}$ to avoid saturation (e.g., caused by overshoot) and/or distortion near the full-scale input. $V_{REFN}$ for the ADC may be set at a level slightly below the low voltage level 1410 of $V_{PRE}$. However, no voltage level of the integrating capacitors falls into the middle portion (shown as the patterned region 1440) of the input range. Therefore, the middle range of the ADC's full-scale input range may not be used at all, and the dynamic range of the ADC may not be fully utilized. To fully utilize the dynamic range of the ADC, the reference levels of the ADC may be changed dynamically such that the input range of the ADC would not include the patterned region 1440.

Figure 14B:
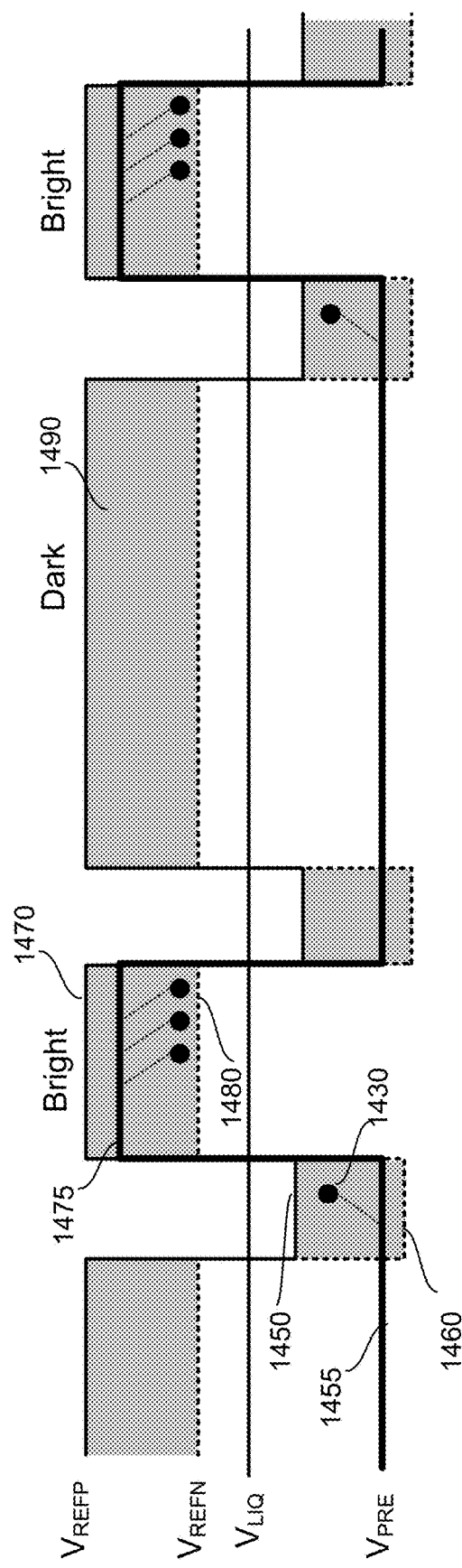
FIG. 14B illustrates variable reference levels for an ADC in a nanopore sensor chip, according to certain aspects of the present disclosure.

FIG. 14B illustrates variable reference levels for an ADC in a nanopore sensor chip. The reference levels include reference levels $V_{REFP}$ and $V_{REFN}$, which determine the full-scale input range and the common mode voltage of the ADC. Reference levels $V_{REFP}$ and $V_{REFN}$ may change with the $V_{PRE}$ signal that cause the nanopore cell to enter bright and dark periods. Therefore, the full-scale input range and/or the common mode of the ADC may be different during the bright and dark periods. In this manner, the output voltage signals of the nanopore cells may better fit within the full-scale input range of the ADC, rather than distributed only within certain narrow ranges of the full-scale input range of the ADC.

For example, as shown in FIG. 14B, to capture a data sample 1430 in the dark period, $V_{REFP}$ may be set to a level 1450 below $V_{LIQ}$. $V_{REFN}$ may be set to a level 1460 below the low voltage level 1455 of $V_{PRE}$, such that the input range of the ADC (shown as the shaded region) only includes regions below $V_{LIQ}$ and between level 1450 and 1460, but does not include the region above level 1450 where no voltage level of the integrating capacitors falls within. To capture data samples in the bright period, $V_{REFP}$ may be set to a level 1470 above the high voltage level 1475 of $V_{PRE}$, and $V_{REFN}$ may be set to a level 1480 above $V_{LIQ}$. Therefore, the input range of the ADC (shown as the shaded region) may only include regions above $V_{LIQ}$ and between levels 1470 and 1480, but does not include the region below level 1480 where no voltage level of the integrating capacitors falls within. The same reference setting may be used during the dark period 1490 of a group when no data samples are captured from nanopore cells in the group and data samples are captured from nanopore cells in other groups that are in the bright period.

In this way, the input range (and the common mode input) of the ADC may be dynamically changed to include only the ranges that the voltage levels of the integrating capacitors may fall in. Therefore, the voltage levels within the input range can be resolved with the maximum possible resolution of the ADC.

VI. Example Method of Increasing Sampling Rate Per Cell

Figure 15:
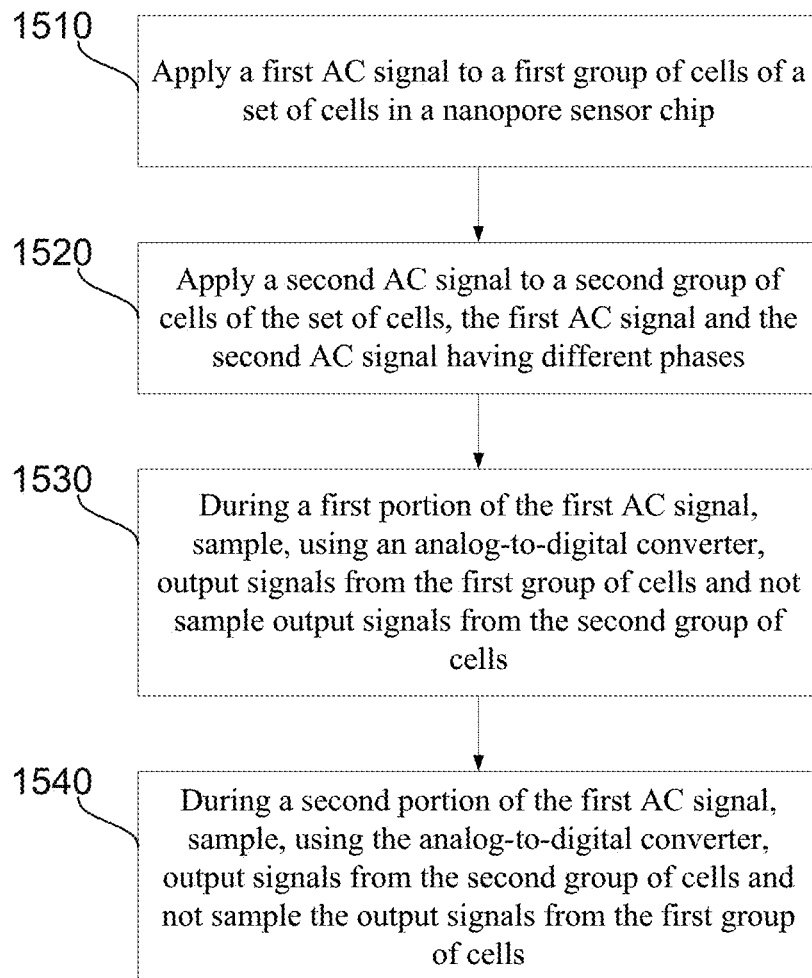
FIG. 15 is a flow chart illustrating an example method of nucleic acid sequencing using a sensor including a set of cells, according to certain aspects of the present disclosure.

FIG. 15 is a flow chart 1500 illustrating an example method of nucleic acid sequencing using a sensor including a set of cells, according to certain aspects of the present disclosure. The method illustrated by flow chart 1500 can apply AC signals with different phases to different groups of nanopore cells in a nanopore sensor chip. As a result, when some nanopore cells are in the dark period, some other nanopore cells are in the bright period and being sampled by a shared sampling and conversion circuit. Thus, the method can reduce the number of cells being serviced by the sampling and conversion circuit at any instant in time, and thus increase the sampling rate per cell without using a faster data sampling and conversion circuit.

At block 1510, a first circuit, such as circuit 622 of FIG. 6 may apply a first AC signal to a first group of cells of a set of cells in a nanopore sensor chip. As described above with respect to FIG. 10, the set of cells in the nanopore sensor chip may be organized into multiple groups, where each group may be independent from other group and have a corresponding circuit for applying an AC signal to the first group of nanopore cells. The AC signal may be a rectangular wave and may have a selected duty cycle. The AC signal may be applied to a working electrode of each nanopore cells in the group, for example, working electrode 402 of nanopore cell 400 in FIG. 4 or working electrode 602 in FIG. 6.

At block 1520, a second circuit may apply a second AC signal to a second group of cells of the set of cells. In some embodiments, the first AC signal and the second AC signal may have different phases and may be derived from a same signal source by different delays. In some embodiments, the first AC signal and the second AC signal may also be different in at least one of amplitude, duty cycle, or frequency.

At block 1530, during a first portion of the first AC signal, the first group of cells may be in the bright period, and an analog-to-digital converter may sample output signals from the first group of cells. During the same time period, the second group of cells may be in the dark period due to the phase difference between the first AC signal and the second AC signal, and the output signals from the second group of cells may not be sampled by the analog-to-digital converter. Thus, during the first portion of the first AC signal, the analog-to-digital converter may only serve the first groups of cells.

At block 1540, during a second portion of the first AC signal, the first group of cells may be in the dark period, and the analog-to-digital converter may not sample output signals from the first group of cells. During the same time period, the second group of cells may be in the bright period, and the output signals from the second group of cells may be sampled by the analog-to-digital converter. Thus, during the second portion of the first AC signal, the analog-to-digital converter may only serve the second groups of cells. In some embodiments as shown in FIG. 11, there may not be overlap between the bright period of the first group of cells and the bright period of the second group of cells. In other embodiments as shown in FIG. 13, the bright period of the first group of cells and the bright period of the second group of cells may partially overlap, and different schemes may be used to determine how the output signals from the two groups of cells may be sampled by the analog-to-digital converter, as described above with respect to FIG. 13.

It is noted that even though FIG. 15 describes the data processing as a sequential process, many of the operations can be performed in parallel or concurrently. In addition, the order of the operations may be rearranged. An operation may have additional steps not included in the figure. Some operations may be optional, and thus may be omitted in various embodiments. Some operations described in one block may be performed together with operations at another block. For example, some operations may be performed in parallel. Furthermore, embodiments of the methods may be implemented in hardware, software, firmware, middleware, microcode, hardware description languages, or any combination thereof.

VII. Computer System

Figure 16:
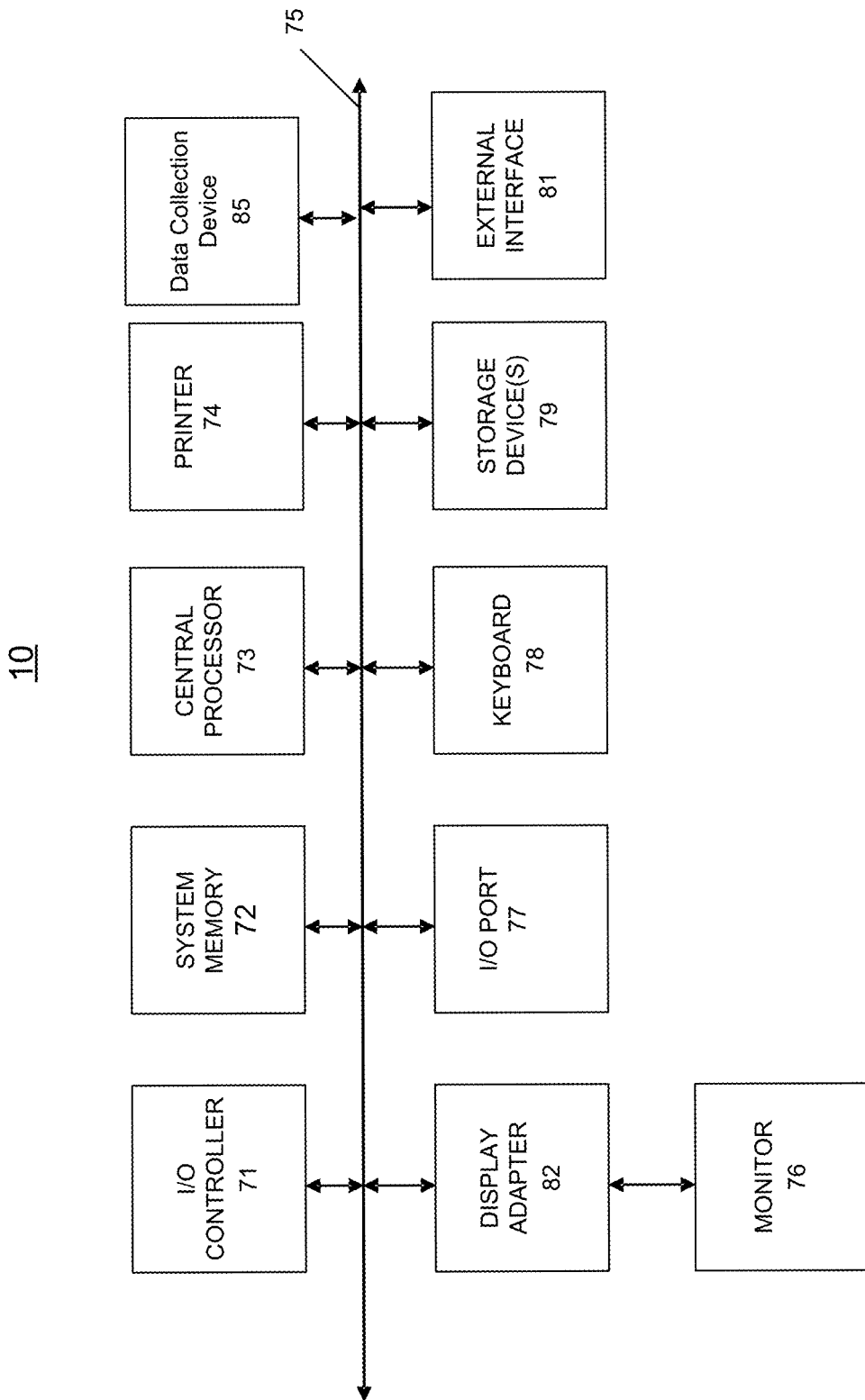
FIG. 16 is a block diagram of an example computer system usable with system and methods, according to certain aspects of the present disclosure.

Any of the computer systems mentioned herein may utilize any suitable number of subsystems. Examples of such subsystems are shown in FIG. 16 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 16 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81, by an internal interface, or via removable storage devices that can be connected and removed from one component to another component. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover reference to a "first" or a "second" component does not limit the referenced component to a particular location unless expressly stated.

All patents, patent applications, publications, and descriptions mentioned herein are incorporated by reference in their entirety for all purposes. None is admitted to be prior art.

What is claimed is:

1. A method for generating sequencing data from a sequencing chip, the method comprising:
   applying a first alternating current (AC) signal to a first group of cells of the sequencing chip;
   applying a second AC signal to a second group of cells of the sequencing chip simultaneously with the application of the first AC signal to the first group of cells, wherein the first AC signal and the second AC signal are out of phase such that, when one of the first group of cells or the second group of cells are in a bright period that generates sequencing data, the other group of cells are in a dark period that does not generate sequencing data; and
   sampling the generated sequencing data from cells in the bright period at a bright period sampling rate.

2. The method of claim 1, further comprising:
   sampling the cells in the dark period at a dark period sampling rate, wherein the bright period sampling rate is greater than the dark period sampling rate.

3. The method of claim 2, wherein the dark period is only sampled to collect data for normalizing the sequencing data sampled in the bright period.

4. The method of claim 1, wherein both the first AC signal and the second AC signal comprise a constant voltage applied to a working electrode of a respective cell of the sequencing chip and a varying voltage applied to a counter electrode of the sequencing chip such that a difference in voltage between the working electrode and the counter electrode has a first polarity in the bright period and a second polarity in the dark period, and wherein the first polarity is opposite the second polarity.

5. The method of claim 4, wherein the varying voltage is configured to alternate between a first voltage level that is greater than the constant voltage applied to the working electrode and a second voltage level that is less than the constant voltage applied to the working electrode.

6. The method of claim 4, wherein the varying voltage is applied to a first common counter electrode for the first group of cells and a second common counter electrode for the second group of cells.

7. The method of claim 1, wherein both the first AC signal and the second AC signal comprise a constant voltage applied to a counter electrode of a respective group of cells of the sequencing chip and a varying voltage applied to a working electrode of the sequencing chip such that a difference in voltage between the working electrode and the counter electrode has a first polarity in the bright period and a second polarity in the dark period, wherein the first polarity is opposite the second polarity.

8. The method of claim 7, wherein the constant voltage is applied to a single common counter electrode for both the first group of cells and the second group of cells.

9. The method of claim 7, wherein the varying voltage is configured to alternate between a first voltage level that is greater than the constant voltage applied to the counter electrode and a second voltage level that is less than the constant voltage applied to counter electrode.

10. The method of claim 9, further comprising:
    controlling a switch of each cell of the first group of cells and the second group of cells to alternately connect the working electrode to the first voltage level and the second voltage level to apply the varying voltage to the working electrode.

11. The method of claim 1, wherein each of the first AC signal and the second AC signal comprises a first periodic signal applied to a counter electrode of the sequencing chip and a second periodic signal applied to a working electrode of the sequencing chip, wherein the first periodic signal and the second periodic signal are characterized by different respective frequencies.

12. The method of claim 1, wherein the first AC signal has a duty cycle equal to or less than 50% such that the bright period is equal to or shorter in duration than the dark period for the first group of cells.

13. The method of claim 1, wherein the first AC signal has a duty cycle equal to or greater than 50% such that the bright period is equal to or greater in duration than the dark period for the first group of cells.

14. The method of claim 1, wherein both the first AC signal and the second AC signal are rectangular waves.

15. The method of claim 1, wherein the sampling is performed using a sampling circuit that comprises a capacitor in electrical communication with a cell electrode and an analog-to-digital converter.

16. The method of claim 1, wherein the sampling is performed using a sampling circuit that comprises an analog-to-digital converter, the method further comprising:
    dynamically changing a reference level setting for the analog-to-digital converter based on phases of the first AC signal provided to the first group of the cells and phases of the second AC signal provided to the second group of the cells.

* * * * *